United States Patent [19]

Mitsuhashi et al.

[11] Patent Number: 4,816,445
[45] Date of Patent: Mar. 28, 1989

[54] CRYSTALLINE ALPHA-MALTOSE

[75] Inventors: Masakazu Mitsuhashi; Shuzo Sakai; Toshio Miyake, all of Okayama, Japan

[73] Assignee: Kabushiki Kaisha Hayashibara Seibutsu Kagaku Kenkyujo, Okayama, Japan

[21] Appl. No.: 739,316

[22] Filed: May 30, 1985

[30] Foreign Application Priority Data

Jun. 21, 1984 [JP] Japan .................................. 59-128282
Jul. 26, 1984 [JP] Japan .................................. 59-156744
Aug. 13, 1984 [JP] Japan .................................. 59-169118
Apr. 11, 1985 [JP] Japan .................................. 60-77029

[51] Int. Cl.⁴ .......................... C13K 7/00; C12G 3/00
[52] U.S. Cl. ...................................... 514/53; 127/30; 127/38; 536/102
[58] Field of Search .................... 514/53; 536/102; 127/30, 38

[56] References Cited

U.S. PATENT DOCUMENTS 3,793,461 2/1974 Yuen ...................................... 514/53
4,279,931 7/1981 Verwaerde et al. ................... 127/38
4,595,418 6/1986 Yoshino ................................. 127/38
4,652,640 3/1987 Sakai et al. ............................ 536/127

FOREIGN PATENT DOCUMENTS 55-20717 2/1980 Japan ...................................... 514/53
56-30911 3/1981 Japan ...................................... 514/53
1232645 5/1971 United Kingdom .
1285352 8/1972 United Kingdom .
2012767B 5/1982 United Kingdom .

OTHER PUBLICATIONS

Cereal Science Today, vol. 17, pp. 180–184 and 186–188 (1972).

Primary Examiner—Ronald W. Griffin
Attorney, Agent, or Firm—Browdy and Neimark

[57] ABSTRACT

A crystalline alpha-maltose with an alpha-maltose isomer content of 55% or higher is prepared by the process comprising preparing a high-concentration syrup, with a moisture content lower than 10 w/w %, from a high-purity maltose with a maltose content of 85% or higher; crystallizing alpha-maltose from the syrup at a temperature within the range of 50°–130° C. in the presence of seed crystal; and recovering the resultant crystalline alpha-maltose with an alpha-maltose isomer content of 55% or higher. The crystalline alpha-maltose is superior to crystalline beta-maltose hydrate in solubility and dispersibility in aqueous media. The crystalline alpha-maltose is a suitable maltose material for food products and pharmaceuticals. A ready-mix-type parenteral hyperalimentation which is highly resistant to browning and alteration is prepared with the crystalline alpha-maltose.

47 Claims, 6 Drawing Sheets

CRYSTALLINE ALPHA-MALTOSE

FIELD OF THE INVENTION

The present invention relates to a crystalline alpha-maltose, and its production and uses. More particularly, it relates to a crystalline alpha-maltose having an alpha-maltose isomer content of 55% or higher, and its production and uses.

DEFINITIONS

The percentages as used herein are given by weight based on the weight of the dry solids, unless specified otherwise.

The "part(s)" as used herein is given by weight.

The wording "alpha-maltose isomer content" means the percentage of the alpha-form maltose, an optical isomer of maltose, to the total maltose content, based on the weight of the dry solids.

DESCRIPTION OF THE PRIOR ART

Sucrose has a large consumption for foodstuffs. Sucrose, however, has the disadvantages that its excessive sweetness does not necessarily appeal to consumer; that it is one cause of cariogenicity; and that its excessive ingestion may increase blood cholesterol level.

To overcome these disadvantages of sucrose, recently non-sucrose sweeteners has been proposed. In particular, commercialization of "SUNMALT®", a pulverulent crystalline beta-maltose hydrate, a product of Hayashibara Co., Ltd., Okayama, Japan, has revealed that crystalline beta-maltose hydrate shows lower sweetening power and cariogenicity than sucrose, as well as that its flavor and taste excellently appeal to consumer. Thus, a great amount of crystalline beta-maltose hydrate is used as an epochal sweetener.

Crystalline beta-maltose hydrate, however, renders the foodstuff processings very complicated or troublesome. So far the use of maltose in low-moisture content processed foods including chocolate has been deemed very difficult, as clearly described, e.g. in Japan Patent Publication No. 26,303/83 (column 3, lines 2–5) that maltose is not practically used in chocolate because it disturbs chocolate processing, and Japan Patent Kokai No. 31,650/84 (column 3, lower corner, lines 11–12) describes that maltose is unfavorable for chocolate manufacture. As an attempt to overcome these difficulties, Japan Patent Publication No 26,303/83 proposes a pulverulent mixture of crystalline sucrose and crystalline beta-maltose hydrate, e.g. "SUNMALT®"; and Japan Patent Kokai No. 31,650/84 describes the comparison of several pulverulent crystalline beta-maltose hydrate products on oil holding capacity and proposes the use of a product exhibiting an oil holding capacity lower than 80. Even with these proposals, chocolate preparation with pulverulent crystalline beta-maltose hydrate is still very difficult. Thus, such chocolate has not been commercialized.

We found that one of major cause rendering the manufacture of a low-moisture content processed food with pulverulent crystalline beta-maltose hydrate very difficult is the inferior work efficiency attained with pulverulent crystalline beta-maltose hydrate: Such manufacture essentially includes a step wherein a pulverulent crystalline saccharide is homogenously pulverized together with or dispersed into other food material(s) by a suitable procedure, e.g. pulverizing, dividing, roll-milling, kneading, mixing, etc. In addition, this step must be carried out in such a manner that a substantial amount of the pulverulent crystalline saccharide does not dissolve in an aqueous medium. Thus, pulverulent crystalline beta-maltose hydrate results in obstacles in these steps, e.g. increase in viscosity, formation of "dama (an undissolved powder mass)", occurrence of "suberigensho (a sliding phenomenon)", etc., and these obstacles render homogenous pulverization and dispersion of pulverulent crystalline beta-maltose hydrate very difficult.

In a processed food having a higher moisture content using pulverulent crystalline beta-maltose hydrate, the employment of any effective but complicated procedure is essential to homogenously incorporate pulverulent crystalline beta-maltose hydrate into said processed food because pulverulent crystalline beta-maltose hydrate relatively slowly dissolves in moist food materials. For example, in the manufacture of butter cream, pulverulent crystalline beta-maltose hydrate and sucrose are dissolved in a small amount of water to prepare a saccharide solution which is then mixed with a whipped butter under stirring. In mashmallow, pulverulent crystalline beta-maltose hydrate and sucrose are dissolved with a small amount of water to prepare a saccharide solution which is then whipped by heating along with gelatin predissolved in a hot water. In the manufacture of "gyuhi (a rice cake)", pulverulent crystalline beta-maltose hydrate and sucrose are dissolved with a small amount of water to prepare a saccharide solution which is then mixed and heated with gelatinized starch paste. "An (a bean-paste)" is manufactured by dissolving pulverulent crystalline beta-maltose hydrate and sucrose with a small amount of water to prepare a saccharide solution, mixing the saccharide solution with "nama-an (a raw bean paste)", and concentrating the resultant mixture with heating and stirring. In alcoholic seasoning for "zozyo-shu (a kind of synthetic sake)", ethanol, about 30 v/v %, is placed in a tank, added with pulverulent crystalline beta-maltose hydrate and seasonings, and dissolved either by (1) mixing with a stirrer for about thirty minutes, or (2) allowing to stand overnight and then stirring with a paddle.

Accordingly, development of a novel maltose product easily disolvable and dispersible in these food materials was in a great need.

A similar need is found in a ready-mix-type parenteral hyperalimentation.

Parenteral hyperalimentation directed to intravenous injection or intubation feeding are widely supplied to those to whom ingestions in normal form are restricted, e.g. patients, convalescent or infirm persons. Generally, parenteral hyperalimentation inevitably has the disadvantages that their container, packaging and transportation are costly, as well as that they must be either stored at a low temperature or limited in effective period because their effective components are liable to cause alteration and/or deterioration. To overcome these problems of parenteral hyperalimentation, lately ready-mix-type parenteral hyperalimentations are used. As disclosed, e.g. in Japan Patent Kokai No 61,310/81 or Japan Patent Kokai No. 128,711/81, glucose is generally used as the calorie source for ready-mix-type parenteral hyperalimentation. Although glucose has the advantage that it is directly utilized in the body, it is disadvantageous because of supplying only a relatively low calorie per administration since isotonic concentration is attained with a small amount of glucose, e.g. 5 w/w %.

As an attempt to overcome this disadvantage of glucose, Japan Patent Kokai No. k20,174/79 proposes a ready-mix-type parenteral hyperalimentation containing maltose. The osmotic pressure attained with an amount of maltose is one-half of that attained with the same amount of glucose. Thus, maltose is much more favorable than glucose because maltose solution can supply 2-fold calorie than does glucose solution with the same osmotic pressure. Upon diligent investigations for ready-mixt-type parenteral hyperalimentation, we unexpectedly found that commercialized crystalline beta-maltose hydrate is disadvantageous because it is low in solubility but is highly liable to cause browning and alteration when stored in a container. Because of these reasons, a satisfactory ready-mix-type parenteral hyperalimentation can not be provided with crystalline beta-maltose hydrate.

We investigated various means to overcome these disadvantages of maltose in conventional foodstuffs and pharmaceuticals. As the result, we found that these disadvantages can be overcome with a crystalline alphamaltose, in particular, that has an alpha-maltose isomer content of 55% or higher.

Crystalline alpha-maltose, however, has been unavailable even as chemical reagent; to say nothing as food-grade.

J.E. Hodge et al. report a crystalline 3:1 or 4:1 alpha/-beta-complex of maltose in *Cereal Science Today*, Vol.17, No.7, pp.180-188 (1972).

To produce such crystalline complex, the following procedures are proposed by the authors:

(1) a procedure wherein a crystalline beta-maltose hydrate (m.p. 121°-125° C.) is heated at 120° C. under atmospheric pressure for one day to convert it into a crystalline alphamaltose; (2) a procedure wherein a viscous syrup, obtained by dehydrating a 60 w/w % aqueous maltose solution at 80°-100° C., is crystallized in the presence of seed crystal, washed with methanol, and filtered to obtain a crystalline alphamaltose in the yield of 70%; and (3) a procedure wherein amorphous maltose beads are refluxed in either anhydrous maltose or anhydrous isopropanol overnight to obtain a crystalline alpha-maltose.

Procedure (1) leads to an undesirable coloration of the resultant crystalline alpha-maltose, more particularly, to a coloring degree of 3.5 in terms of the absorbance difference (A420-720) calculated from the absorbances at wave lengths of 420 and 720 nm in 30 w/v % aqueous solution using 10 cm-cell. We confirmed that this coloring degree is approximately 50-folds of the material crystalline beta-maltose hydrate. Thus, the resultant crystalline alpha-maltose is unmarketable as sweetener, and this procedure is not practical for industrial-scale production.

Procedure (2) leads to a relatively low yield of crystalline alpha-maltose, as well as consuming a large amount of methanol. In view of production cost, food sanitation, and fire prevention, this procedure is undesirable for industrial-scale production.

In view of production cost, food sanitation, and fire prevention, procedure (3) is unemployable for industrial-scale production because it consumer large quantity of organic solvent.

SUMMARY OF THE INVENTION

We investigated various means to establish an industrial-scale production of a crystalline alpha-maltose, in particular, a high-yield production of a high-quality crystalline alpha-maltose having a lower coloring degree, desirably, a pulverulent crystalline alpha-maltose, and its uses in foodstuffs and pharmaceuticals.

As the result, we found that such crystalline alpha-maltose is easily obtainable by a process comprising preparing a high-concentration syrup, with a moisture content lower than 10 w/w %, from a high-purity maltose with a maltose content of 85% or higher; crystallizing alpha-maltose from the syrup at a temperature within the range of 50°-130° C. in the presence of seed crystal; and recovering the resultant crystalline alpha-maltose with an alpha-maltose isomer content of 55% or higher.

We confirmed that the crystalline alpha-maltose can be easily pulverized together with or dispersed into other food materials to homogeneity without affecting or modifying conventional manufacturing steps, as well as that a high-quality, tasty foodstuff having a desirably controlled sweetness can be easily manufactured with the crystalline alpha-maltose.

Also was found that the crystalline alpha-maltose:

(1) dissolved more readily than crystalline beta-maltose hydrate; its solubility in an aqueous system being extremely high even at a low temperature;

(2) is superior in affinity to oil and fat to crystalline beta-maltose hydrate; and (3) is less liable to cause browning and/or alteration when kept and stored in an enclosed container, and extremely stable over a long period of storage.

We confirmed that these features facilitate the manufacture of specific pharmaceutical composition, in particular, a ready-mix-type parenteral hyperalimentation, desirably, a dietetically-well-balanced, high-calorie ready-mix-type parenteral hyperalimentation containing oil and/or fat, as well as that the addition of an aqueous medium readily dissolves and disperses the parenteral hyperalimentation to give an emulsion readily utilizable in vivo.

DESCRIPTION OF THE PREFERRED EMBODIMENTS

Figure 1:
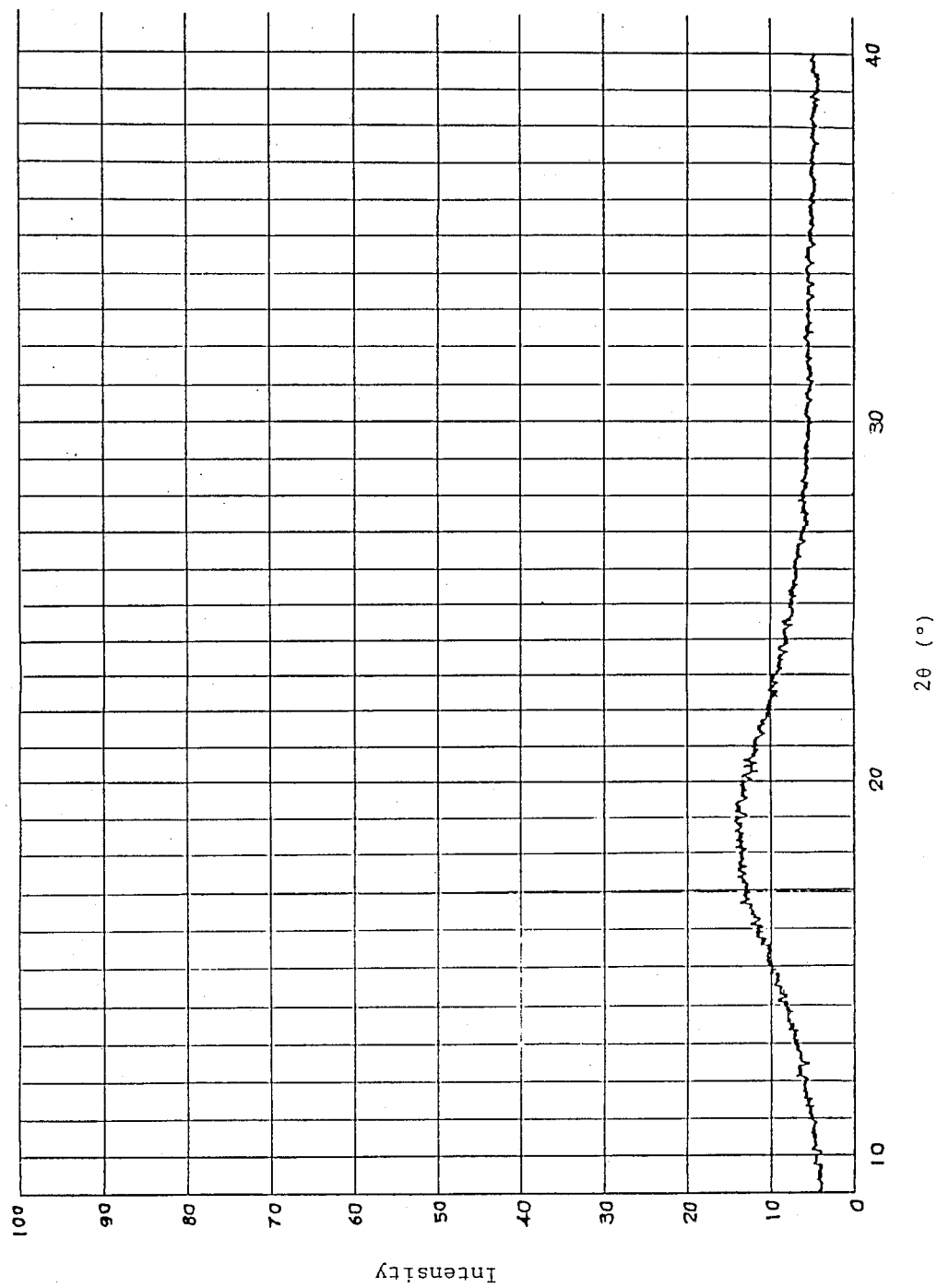
FIG.1 shows an x-ray diffraction spectrum of an amorphous powder with an alpha-maltose of 48.0%.

The maltose material used to produce the crystalline alpha-maltose is a high-purity maltose with a maltose content of 85% or higher. Such maltose material may be a commercialized crystalline beta-maltose hydrate or a high-purity maltose prepared by saccharifying starch in conventional manner: For example, Japan Patent Publication Nos.11,437/81 and 17,078/81 disclose the production of a high-purity maltose, wherein either a gelatinized-or liquefied-starch is subjected to the action of beta-amylase, followed by separation of the resultant maltose from the higher dextrins; and Japan Patent Publication Nos. 13,089/72 and 3,938/84 teach the subjection of a gelatinized- or liquefied-starch to the actions of beta-amylase and a starch-debranching enzyme such as isoamylase or pullulanase.

The maltose content in the high-purity maltose can be augmented by subjecting the saccharide impurities present therein, e.g. maltotriose, to the action of a specific enzyme as disclosed i n Japan Patent Publication No. 28,153/81, 3,356/82, or 28,154/81 to decompose the impurities into maltose. Alternatively, as disclosed in Japan Patent Kokai No. 23,799/83, the saccharide impurities may be removed by fractionating the high-purity maltose with a column of a strongly-acidic cation exchange resin in a salt form. Such fractionation can be carried out with the fixed bed-, moving bed-, or simulated moving bed-method.

The high-purity maltose with a maltose content of 85% or higher is concentrated into a syrup with a moisture content lower than about 10 w/w %, desirably 2.0 w/w % or higher but lower than 9.5 w/w %, which is then added with about 0.01–20% crystalline alpha-maltose seed and crystallized at a temperature within the range of about 50°–130° C. to obtain the objective crystalline alpha-maltose.

We found that a substantial amount of alpha-maltose is not crystallized if the moisture content of a high-purity maltose syrup is 10 w/w % or higher: In particular, with a moisture of 12 w/w % or higher or lower than 25 w/w %, the crystalline alpha-maltose seed is liable to dissolve, but crystalline beta-maltose hydrate may be crystallized. Also was found that a syrup with a moisture content lower than 2.0 w/w % leads to a retarded crystallization.

The desirable crystallization temperature is within the range of 50°–130° C., in particular, 60°–120° C. Crystallization progresses very slowly at a temperature below 50° C., and, therefore, unfavorable for industrial-scale production. A temperature exceeding 130° C. is also unfavorable because such temperature retards the crystallization of alpha-maltose, as well as causing an extreme coloration of the crystallized alpha-maltose.

Thus, the process according to the invention essentially contains a step of crystallizing alpha-maltose while keeping a high-purity maltose syrup with a moisture content lower than 10 w/w % at a temperature within the range of 50°–130° C. in the presence of seed crystal.

Such high-purity maltose syrup can be prepared by dissolving a commercialized crystalline beta-maltose hydrate, with a maltose content of 85% or higher, with a small portion of water, or concentrating in vacuo an aqueous solution of a high-purity maltose with a maltose content of 85% or higher obtained by saccharifying starch. Alternatively, an aqueous solution of a high-purity maltose with a moisture content of 10 w/w % or higher but lower than 35 w/w % may be prepared into syrup droplets with a moisture content lower than 10 w/w % by a suitable procedure such as spray-drying.

Alpha-maltose is generally crystallized from the high-purity maltose syrup in the presence of a crystalline alpha-maltose seed in an amount of 0.001% or more but less than 100%, desirably 0.1% or more but less than 20%. For example, to crystallize alpha-maltose, (1) a high-purity maltose syrup with a moisture content lower than 10 w/w % is kneaded with the seed crystal, or (2) a high-purity maltose syrup with a moisture content of 10 w/w% or higher but lower than 20 w/w % is mixed with the seed crystal, and prepared into, before the seed crystal is lost by dissolution, syrup droplets with a moisture content lower than 10 w/w % by spray-drying. Alternatively, a high-purity maltose syrup with a moisture content of 10 w/w % or higher but lower than 35 w/w % may be prepared into droplets with a moisture content lower than 10 w/w %, which are then allowed to contact with the seed crystal to crystallize alpha-maltose.

Alpha-maltose crystallization can be favorably accelerated by application of a slightly elevated pressure, in particular, about 5 kg/cm2 or higher, at the beginning or in the course of the crystallization. As in the case of extrusion granulation, this is very favorable when the crystallized alpha-maltose is pulverized by applying an elevated pressure or a compression.

We found that the dehydration of the crystal suspension also favorably accelerates alpha-maltose crystallization. Such dehydration can be carried out under atmospheric-, reduced-, or elevated-pressure while allowing the crystal suspension to stand or move.

These acceleration procedures shorten about four-fifth to about two-fifth the period required to obtain an alpha-maltose isomer content of 55% or higher. Furthermore, these procedures increase the production efficiency of crystalline alpha-maltose and extremely decrease the coloration of crystallized alpha-maltose. Thus, these procedures are favorable for industrial-scale production of a high-quality crystalline alpha-maltose. Combined use of these procedures is also favorable. For example, a high-purity maltose syrup with a moisture content lower than 10 w/w % is crystallized in a manner as described above to obtain a crystal suspension which is then prepared into any desirably form e.g. powder, strand, block, etc., and aged by dehydration at a temperature within the range of 50°–130° C. to obtain a crystalline alpha-maltose with an alpha-maltose isomer content of 55% or higher.

Ageing can be desirably continued for about 0.1–24 hours at a temperature within the range of 50°–100° C., or for about 0.5–18 hours at a temperature higher than 100° C. but lower than 130° C. We found that ageing under more vigorous conditions, i.e. at a higher temperature for a longer time, increases the coloration of crystallized alpha-maltose and renders it unfit to sale. Application of an elevated pressure and/or dehydration favorably shortens the ageing time, as well as accelerating alpha-maltose crystallization.

The crystalline alpha-maltose with an alpha-maltose isomer content of 55% or higher is generally prepared into any desirably form such as powder or granule by a suitable procedure. Examples of such procedures includes extrusion granulation, block-pulverization, spray-drying, and fluidized-bed granulation.

In extrusion granulation, for example, a high-purity maltose syrup with a moisture content lower than w/w % is crystallized by kneading together with crystalline alpha-maltose seed at a temperature within the range of 50°–130° C. to obtain a crystal suspension with an alphamaltose isomer content exceeding 48%, which is then fed to an extrusion granulator. The resultant granular suspension or granular solid is then aged by dehydration at a temperature within the range of 50°–130° C. to obtain a pulverulent crystalline alpha-maltose with an alpha-maltose isomer content of 55% or higher.

Alternatively, a high-purity maltose syrup with a moisture content lower than 10 w/w % is fed to an extrusion granulator without addition of the seed crystal and prepared into syrup droplets which are then allowed to contact with crystalline alpha-maltose seed and aged by dehydration at a temperature within the range of 50°-130° C. to obtain a similar pulverulent crystalline alpha-maltose.

In block-pulverization, for example, a high-purity maltose syrup with a moisture content lower than 10 w/w % is fed to a crystallizer and mixed with crystalline alpha-maltose seed at a temperature of 50°-130° C. to effect crystallization. The resultant crystal suspension with an alphamaltose isomer content exceeding 48% is then poured, for example, into an aluminum tray, and the content is crystallized and solidified within the tray at a temperature within the range of 50°-130° C. The resultant block is pulverized with a shaver or a hammer mill, dehydrated, and screened to obtain a pulverulent crystalline alpha-maltose with an alpha-maltose isomer content of 55% or higher.

In spray-drying, for example, a high-purity maltose syrup with a moisture content of 10 w/w % or higher but lower than 20 w/w % is mixed with crystalline alpha-maltose seed and spray-dried through a high-pressure nozzle or with a rotary disc as soon as possible so that the seed crystal does not dissolve and disappear. The obtained syrup droplets with a moisture content lower than 10 w/w % are then aged by dehydration at a temperature within the range of 50°-130° C. to obtain a pulverulent crystalline alpha-maltose with an alpha-maltose isomer content of 55% or higher.

In fluidized-bed granulation, for example, a high-purity maltose syrup with a moisture content of 15 ww % or higher but lower than 35 w/w % is sprayed towards a fluidized crystalline alpha-maltose, used as the seed crystal, to give syrup droplets with a moisture content lower than 10 w/w %, which are then aged by dehydration at a temperature within the range of 50°-130° C. to obtain a pulverulent crystalline alpha-maltose with an alpha-maltose isomer content of 55% or higher.

A part of the crystalline alpha-maltose thus obtained may be continuously supplied as the seed to the crystallization step for a continuous operation of the present process.

The pulverulent crystalline alpha-maltose with an alpha-maltose isomer content of 55% or higher thus obtained is a white, odorless, mildly sweet solid substantially non-hygroscopic and freely-flowing, slightly variable with the particle form, particle size, and alpha-maltose isomer content. The moisture content of the crystalline alpha-maltose is low, generally lower than 5 w/w %, desirably lower than 3 w/w %. The melting point is 130° C. or higher which is far beyond that of crystalline beta-maltose hydrate (i.e. 121°-125° C.). A pulverulent crystalline alpha-maltose with an alpha-maltose isomer content of 60% or higher has a melting point of about 140° C. or higher and a satisfactory fluidity, but does not cause undesirably caking and consolidation.

As detailed hereinafter, the crystalline alpha-maltose is favorably usable as the saccharide material for foodstuffs, cosmetics, pharmaceuticals, chemicals, etc.

As a seasoning to sweeten foodstuffs, the crystalline alpha-maltose of the invention can be used intact or along with, for example, one or more additional sweeteners such as pulverulent starch sugar, glucose, isomerized sugar, sucrose, honey, maple sugar, sorbitol, maltitol, dihydrocharcone, stevioside, alpha-glycosyl stevioside, sweet substance derived from *Momoridca grosvenori* Swingle, glycyrrhizin, thaumatin, L-asparatyl L-phenylalanine methyl ester, saccharin, glycine, or alanine; and/or filler such as dextrin, starch or lactose. The pulverulent crystalline alpha-maltose can be molded, intact or after mixing with filler, vehicle and/or binder, into any desirably form, e.g. tablet, rod, plate, cube, etc., prior to its use.

We found that a large quantity of the crystalline alpha-maltose is instantly dissolvable in various solutions of organic acid or salt, as well as in water. Of course, the crystalline alpha-maltose imparts mild sweetness, body, gloss, viscosity and moisture to foodstuffs, but has no fear of inducting dental caries or of increasing blood cholesterol level, which are inherently characterized in maltose. Thus, the crystalline alpha-maltose can be favorably used to manufacture foodstuffs, cosmetics and pharmaceuticals.

Since a quantity of the crystalline alpha-maltose is instantly dissolvable in water or various aqueous solutions, it can be easily dissolved, by directly kneading, in moist food material, e.g. aqueous sol, halfsol and gel, such as juice, honey, jam, egg, milk, yohgurt, gelatinized starch paste, nut paste, butter, margarine, fish meat paste, "nama-an (a raw bean paste)", miso, dough, etc., which are used to manufacture processed foods with a moisture content of 10 w/w % or higher. This shortens and/or simplifies the manufacturing steps of such processed foods. In the processed foods thus obtained, the water activity is significantly lowered, and the retrogradation of gelatinized amylaceous component is retarded when starch is incorporated thereinto. We found that these extremely prolong the shelf lives of the processed foods.

We also found that, unlike the pulverulent maltose syrup as disclosed, for example, in Japan Patent Publication No. 48,198/77, a quantity of the crystalline alpha-maltose is instantly dissolvable even in 40 v/v % aqueous ethanol solution. By utilizing the above mentioned advantages of imparting mild sweetness, body and viscosity, and this feature, the crystalline alpha-maltose can be favorably used as the seasoning saccharide for alcoholic beverages. Thus, the crystalline alpha-maltose is extremely favorable to manufacture alcoholic beverages such as liquor, synthetic sake, and "zozyo-shu".

We unexpectedly found that the crystalline alpha-maltose exhibits a high affinity to oil and fat though it is a hydrophilic substance. This facilitates the manufacture of, for example, chewing gum, chocolate, cream paste, spread, powdered oil and fat, powdered oil-soluble spice, granule of oil-soluble coloring agent, convenient soup, oil-soluble vitamin preparation, and tablet of oil-soluble hormone or unsaturated higher fatty acid, which contain an oil-soluble substance, e.g. oils and fats such as soybean oil, rapeseed oil, mustard oil, sesame oil, safflower oil, palm oil, cacao butter, beef tallw, lard, chicken oil, marine oil, and hardened oil; oil-soluble spices such as citrus essential oil, flower essential oil, spice oil, peppermint oil, spearmint oil, cola nut extract, and coffee extract; oil-soluble coloring agents such as beta-carotin, paprika pigment, annotto pigment, and chlorophyll; oil-soluble vitamins such as liver oil, vitamin A, vitamin B2 lactate, vitamin E, vitamin K, or vitamin D; oil-soluble hormones such as estrogen, progesterone, or androgen; unsaturated higher fatty acids such as linoleic acid, linolenic acid, arachidonic acid, eicosapentaenoic acid, and docosahexaenoic acid.

The mild sweetness of the crystalline alpha-maltose harmonizes with sour-, salty-, astringent-, delicious- and bitter-tastes of the other substances, and the crystalline alpha-maltose per se is highly acid- and heat-resistant. Thus, in addition to the above mentioned special uses, the crystalline alpha-maltose is favorably usable to sweeten foodstuffs in general or to improved the taste qualities thereof.

The crystalline alpha-maltose is freely usable to manufacture seasonings, e.g. soy sauce, powdered soy sauce, miso, powdered miso, "moromi (an unrefined sake)", "hishio (a salted meat)", "furikake (a seasoned fish meal)", mayonnaise, dressing, vinegar, "sanbai-zu (a sauce of sake, soy, and vinegar)", "funmatsu-sushi-no-moto (a premix for seasoning sushi)", "chaka-no-moto (an instant mix of Chinese dish)", "tentsuyu (a sauce for Japanese deep-fat fried food)", "mentsuyu (a sauce for Japanese vermicelli)", sauce, catsup, "yakini-ku-no-tare (a sauce for japanese roast meats)", curry roux, instant stew mix, instant soup mix, "dashi-no-moto (an instant stock mix)", mixed seasoning, "mirin (a sweet sake)", "shin-mirin (a synthetic mirin)", table sugar, coffee sugar, etc., as well as to sweeten or improve the taste qualities of foodstuffs, e.g. Japanese-style confectioneries such as "senbei (a rice cracker)", "araremochi (rice-cake pellets)", "okoshi (a millet-and-rice cake)", "kyuhi (a rice paste)", rice paste, "manju (a bun with a bean-jam filling)", "uiro (a sweet rice jelly)", "an (a bean jam)", "yokan (a sweet jelly of beans)", "mizuyokan (a soft adzuki-bean jelly)", "kingyoku (a kind of yokan)", jelly, pao de Castella (a sponge cake), and "amedama (toffees)"; confectioneries and bakery products such as bun, biscuit, cracker, cookie, pie, pudding, butter cream, custard cream, cream puff, waffle, sponge cake, doughnut, chocolate, chewing gum, caramel, and candy; frozen desserts such as ice cream, and shurbet; syrups such as "kajitsu-no-syrup-zuke (a preserved fruit)", and "kori-mitsu (a sugar syrup for shaved ice)"; pastes such as flour paste, peanut paste, fruit paste; processed fruits and vegetables such as jam, marmalade, and "syrup-zuke (fruit pickles)", "toka (a sugared fruit)"; pickles and pickled products such as "fuku-jin-zuke (red colored radish pickles)", "bettara-zuke (fresh radish pickles)", "senmai-zuke (fresh radish pickles)", and pickled scallions; premixes for pickles and pickled products such as "takuan-zuke-no-moto (a premix for pickled radish)", and "hakusai-zuke-no-moto (a premix for fresh white rape pickles)"; meat products such as ham, and sausage; fish meat products such as fish ham, fish sausage, "kamaboko (a steamed fish paste)", "chikuwa (a kind of fish paste)", and "tempura (a Japanese deep-fat fried food)"; "chinmi (relish)" such as "uni-no-shiokara (salted guts of sea urchin)", "ika-no-shiokara (salted guts of cuttlefish)", "su-konbu (a processed tangle)", "saki-surume (dried cuttlefish strips)", and "fugu-no-mirinboshi (a dried mirin-seasoned swellfish)"; "tsukudani (foods boiled down in soy)" such as those of laver, edible wild plants, dried cuttlefish, fish, and shellfish; daily dishes such as "nimame (cooked beans)", potato salad, and "konbu-maki (a tangle roll)"; milk products; canned and bottled products such as those of meat, fish meat, fruit, and vegetable; alcoholic beverages such as synthetic sake, "zozyo-shu", fruit wine, and liquors; soft drinks such as coffee, cocoa, juice, carbonated beverage, sour milk beverage, and beverage containing a lactic bacterium; instant foodstuffs such as instant pudding mix, instant hot cake mix, juice powder, instant coffee, "sokuseki-shiruko (an instant mix of adzuki-bean soup with rice cake)", and instant soup mix.

The crystalline alpha-maltose may be used for feeds and pet foods directed to domestic animal and fowl, pet animal, fish, honey bee, silkworm, and fish.

In addition, the crystalline alpha-maltose is freely usable to sweeten tobaccos, cosmetics, and pharmaceuticals in solid, paste or liquid form, such as cigar, cigarette, dentifrice, lipstick, lipcream, medicine for internal administration, troche, cod-liver oil drop, oral refreshing agent, cachou, and collutorium, as well as to improve the taste qualities of these products.

The crystalline alpha-maltose is a suitable calorifascient saccharide directed to a ready-mix-type parenteral hyperalimentation because the crystalline alpha-maltose:

(1) exhibits a high solubility in an aqueous system because of its superior hydrophilicity;

(2) exhibits a strong emulsifying power because of its high affinity to oily substance; and (3) is much less liable to cause browning and/or alteration when stored in a closed container.

The crystalline alpha-maltose can be incorporated into the ready-mix-type parenteral hyperalimentation at any time during its manufacturing steps.

If calorie supply is a sole object, a ready-mix-type parenteral hyperalimentation can be prepared simply by enclosing the crystalline alpha-maltose in a container. If a more balanced parenteral hyperalimentation is desirable, then one or more additional nutriments, e.g. other saccharides, proteins, amino acids, oils, fats, vitamins, minerals, etc., can be incorporated along with the crystalline alpha-maltose. The parenteral hyperalimentation may be incorporated with one or more additional substances, e.g. antibiotic, hormone, immune regulator, crude drug extract, antioxidant, coloring agent, emulsifier, filler, etc. When the ready-mix-type parenteral hyperalimentation is to be used for injection or hemodialysis, highly-purified and pyrogen-free materials including the crystalline alpha-maltose should be used. The ready-mix-type parenteral hyperalimentation is generally shaped into powder or granule so that it dissolves as soon as possible.

The high-quality of a fresh preparation can be retained over a long period of time by enclosing it in a container, desirably, a waterproof container. Such enclosure may be carried out while degassing the container or injecting an inert gas such as carbon dioxide, nitrogen, or argon, if necessary.

The ready-mix-type parenteral hyperalimentation can be easily dissolved or emulsified with water or an aqueous solution to give a liquid or an emulsion with the prescribed concentration, after which the resultant liquid or emulsion is administrated into the masculine, vein, or abdominal cavity by a suitable parenteral procedure: e.g. into the masculine, vein, or abdominal cavity by means of injection; into the nasal cavity, esophagus, or stomach by means of intubation feeding; or into the vascular tract by means of dialysis using an artificial kidney. Since the ready-mix-type parenteral hyperalimentation enclosed in a waterproof container can be dissolved in the container by directly adding water or an aqueous solution, a parenteral hyperalimentation in liquid form is easily obtained. When the liquid preparation is to be used for injection or hemodialysis, the osmotic pressure of the preparation should be adjusted to a possible isotonicity by carefully dissolving the ready-mix-type parenteral hyperalimentation.

Since the liquid preparation is readily utilized to give a high calorie upon administration, it is suitable for hyperalimentation to those to whom ingestions in normal form are restricted, such as an infant, weakly person during or after an illness, or person emaciated by a heavy exercise.

In hemodialysis using artificial kidney, the ready-mix-type parenteral hyperalimentation is dissolved in a specific liquid preparation for hemodialysis, prior to its use. Such hemodialysis supplies the nutriments including maltose to the blood, while the waste products in the blood are excreted into the liquid preparation. The maltose supplied to the blood is utilized independently on insulin. The ready-mix-type parenteral hyperalimentation, in particular, to the insulin-deficient persons such as diabetics or glycosuria persons.

The present invention will be further explained with reference to the following experiments.

Experiment 1

Comparison of several maltose materials
Several starch sugar products as listed in Table I, commercialized by Hayashibara Co., Ltd., Okayama, Japan, were used as the material. The syrup product, i.e. "MALSTAR ®" or "HM-75", was placed in an evaporator and evaporated in vacuo to give a moisture content of 4.5 w/w %. The pulverulent crystalline beta-maltose hydrate product, i.e. "SUNMALT ®", "MALTOSE H", "MALTOSE HH", OR "MALTOSE HHH", was dissolved with a small portion of water by heating, placed in an evaporator, and evaporated in vacuo to give a moisture content of 4.5 w/w %.

Figure 2:
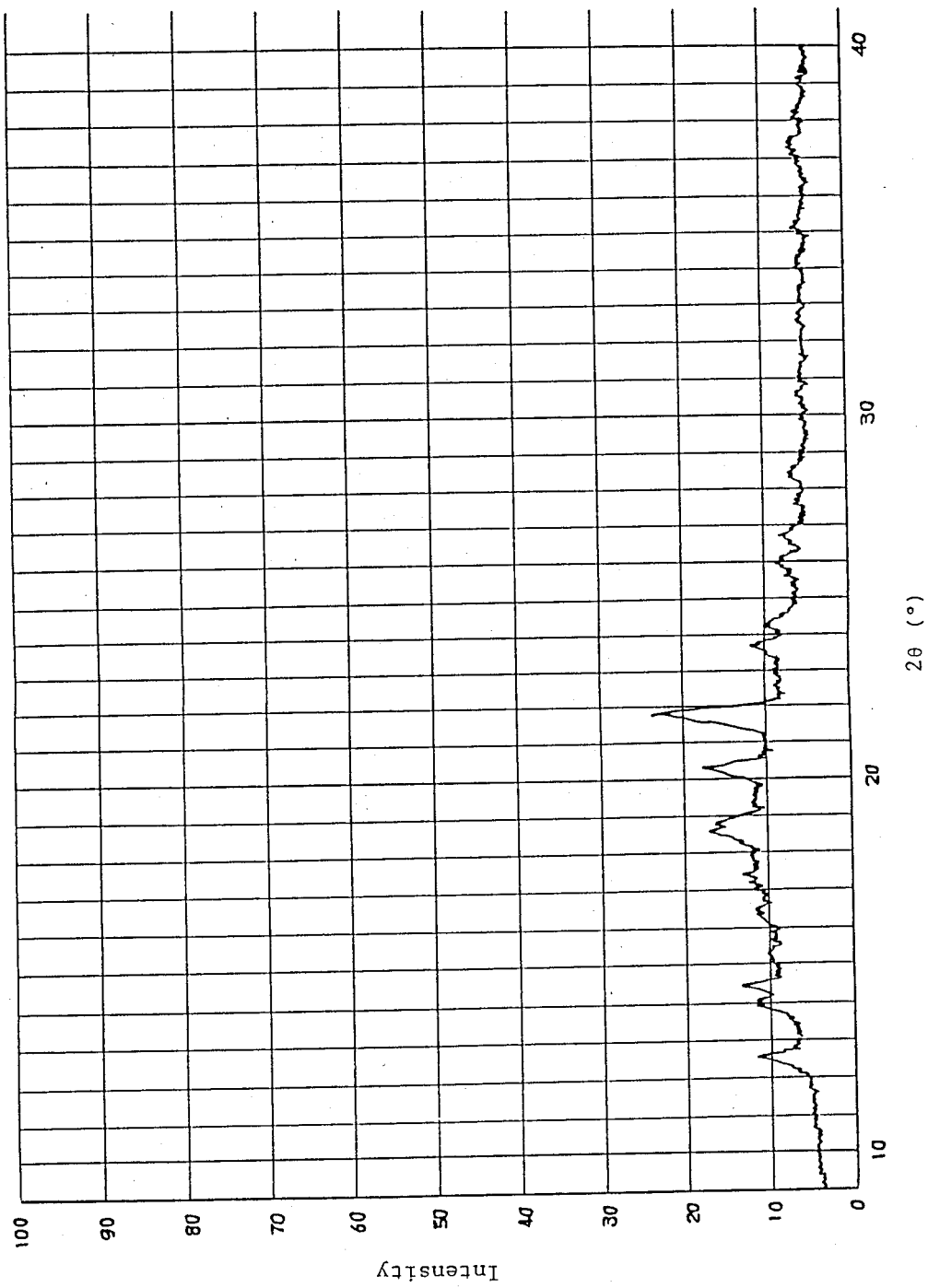
FIG.2 shows an x-ray diffraction spectrum of a crystalline powder with an alpha-maltose content of 55.6%.
Figure 3:
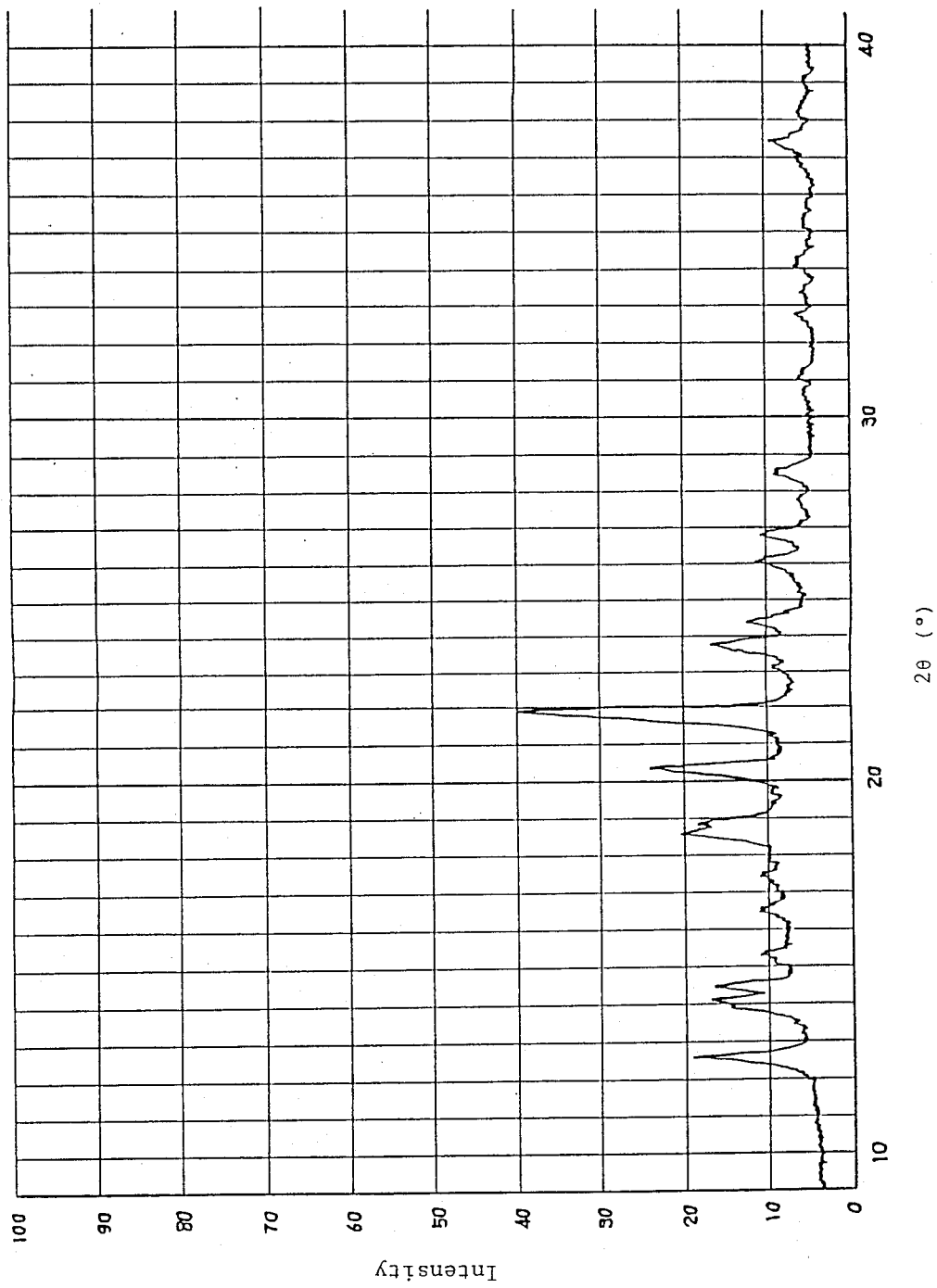
FIG.3 shows an x-ray diffraction spectrum of a crystalline powder with an alpha-maltose content of 61.4%.
Figure 4:
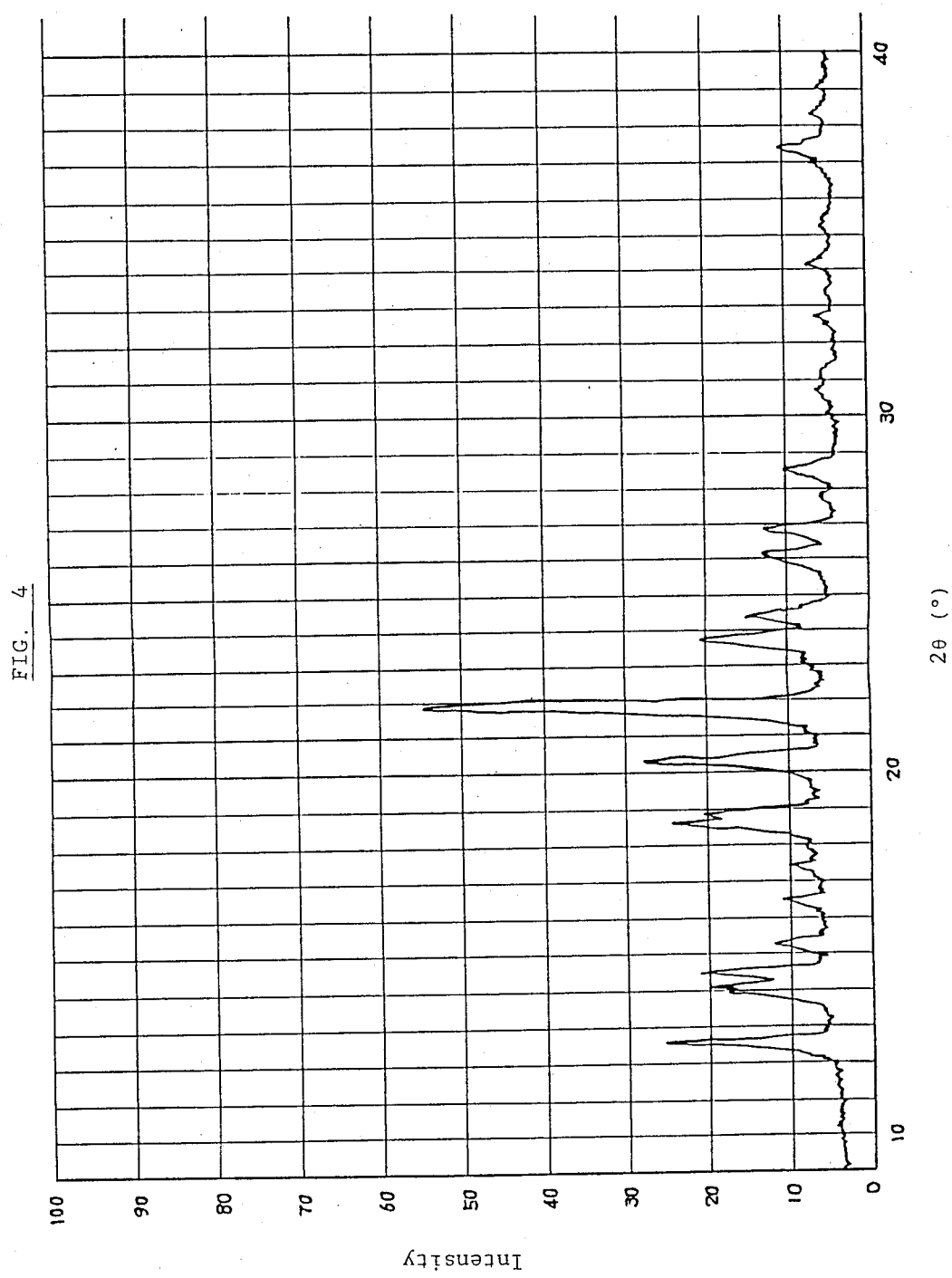
FIG.4 shows an x-ray diffraction spectrum of a crystalline powder with an alpha-maltose content of 68.7%.

The resultant syrup with a moisture content of about 4.5 w/w % was placed in a crystallizer, added with 2% crystalline alpha-maltose seed which had been crystallized and recovered from an about 50 w/v % hot aqueous alcoholic solution of "MALTOSE HHH (a commercialized crystalline high-purity beta-maltose hydrate), and crystallized at 120° C. for twenty minutes. Thereafter, the content was placed in an aluminium tray and aged at 90° C. for sixteen hours. The resultant block was cooled to room temperature and finely divided. The alpha-maltose content in the resultant powder was determined by gas-chromatography as described by C.C Sweeley et al., in *Journal of the Americal Chemical Society*, Vol.85, pp. 2497-2507 (1963). Separately, the powder was subjected to x-ray diffraction analysis using CuKα ray as described by F.H. Stodola et al., in *Journal of the Americal Chemical Society*, Vol.78, pp.2514-2518 (1956) in order check the presence of crystal. The employed x-ray diffractometer was "GEIGERFLEX RAD-II B", commercialized by Rigaku Corporation, Chiyodaku, Tokyo, Japan. The results are given in Table I. The x-ray diffraction spectra are given in FIGs.1-5. FIG.1 shows an x-ray diffraction spectrum of an amorphous powder with an alpha-maltose content of 48%; FIG.2, an x-ray diffraction spectrum of a crystalline powder with an alphamaltose content of 55.6%; FIG.3, an x-ray diffraction spectrum of a crystalline powder with an alpha-maltose content of 61.4%; FIG.4, an x-ray diffraction spectrum of a crystalline powder with an alpha-maltose content of 68.7%; and FIG.5, an x-ray diffraction spectrum of a crystalline powder with an alpha-maltose content of 74.2%.

Figure 6:
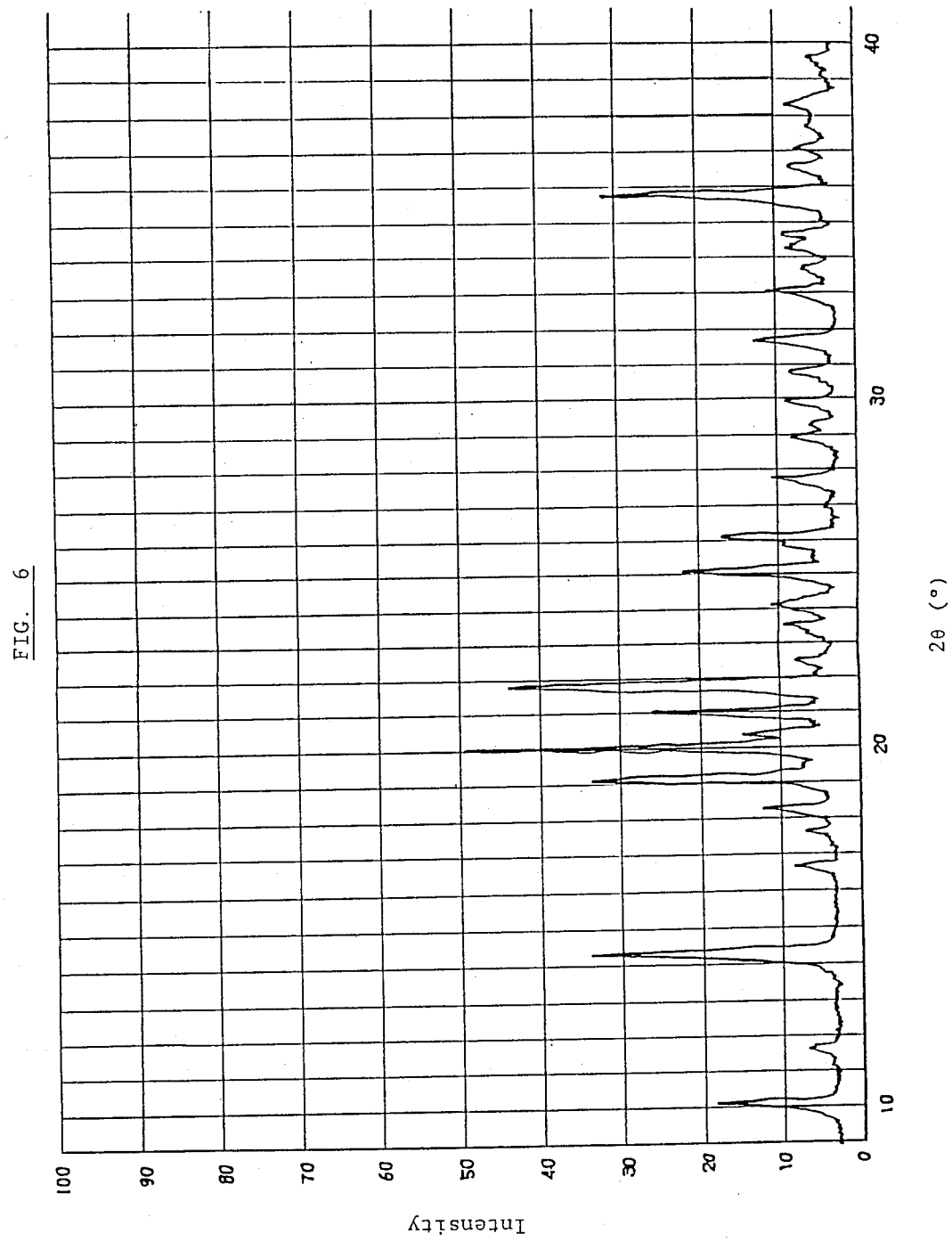
FIG.6 shows an x-ray diffraction spectrum of "MALTOSE HHH (a commercialized pulverulent crystalline beta-maltose hydrate)".

As the control, a portion of "MALTOSE HHH" was dissolved in water by heating, dried in vacuo, and finely divided to obtain an amorphous powder which was then subjected to the x-ray diffraction analysis to obtain a similar x-ray diffraction spectrum as shown in FIG.1. The x-ray diffraction study of "MALTOSE HHH" gave a spectrum as shown in FIG.6.

These x-ray diffraction results evidently confirm that the alphamaltose isomer content required for crystallization is 55% or higher, and that the maltose content of a feasible material maltose is 85% or higher.

As is evident from FIG.4, the x-ray diffraction analysis confirmed that the crystalline alpha-maltose has predominant diffraction angles (2θ) of 12.6°, 20.3°, and 21.9°.

TABLE I

Figure 5:
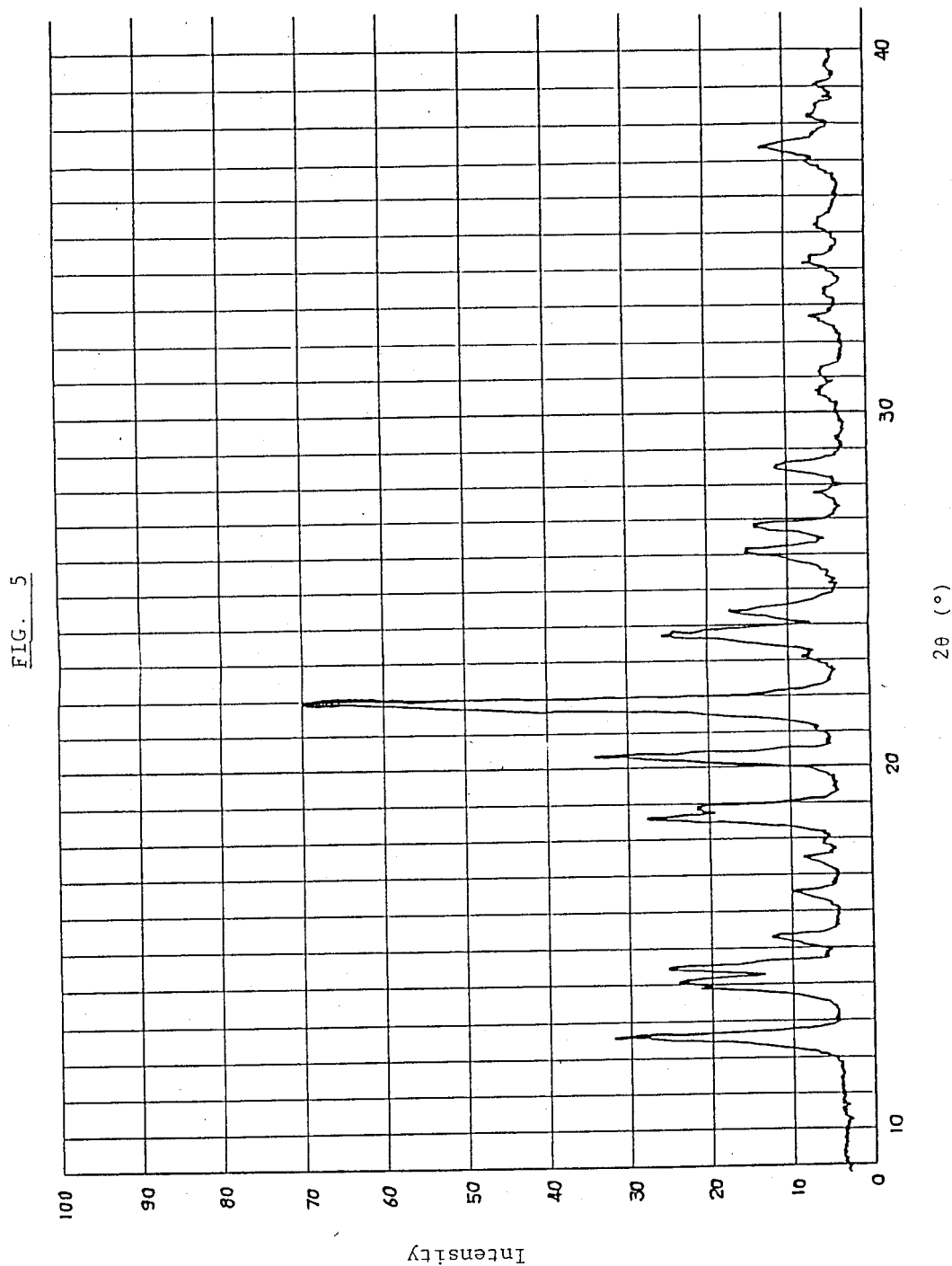
FIG.5 shows an x-ray diffraction spectrum of a crystalline powder with an alpha-maltose content of 74.2%.

| Test No. | Material maltose (Trade name) | Maltose content (%) | Alpha-maltose isomer content (%) | X-ray diffraction Crystal | Diffraction spectrum |
|---|---|---|---|---|---|
| 1 | MALSTAR ® | 68.4 | 48.0 | Absent | FIG. 1 |
| 2 | HM-75 | 79.6 | 48.0 | Absent | FIG. 1 |
| 3 | SUNMALT ® | 85.8 | 55.6 | Present | FIG. 2 |
| 4 | MALTOSE H | 91.5 | 61.4 | Present | FIG. 3 |
| 5 | MALTOSE HH | 96.2 | 68.7 | Present | FIG. 4 |
| 6 | MALTOSE HHH | 99.7 | 74.2 | Present | FIG. 5 |
| 7 | MALTOSE HHH | 99.7 | 48.0 | Absent | FIG. 1 |
| 8 | MALTOSE HHH | 99.7 | 2.3 | Present | FIG. 6 |

Experiment 2

Comparison of affinity to oil and fat

Experiment 2-1

Comparison of oil holding capacity

Fresh specimens (Test Nos. 1-8), prepared by the method in Experiment 1, and Test Nos. 9 and 10, respectively using sucrose and lactose, were pulverized to give a mean particle size of about 45-150 μ, and compared on their oil holding capacity.

The oil holding capacity was determined in a conventional manner as described in Japan Patent Kokai No. 31,650/84: Ten g of rapeseed oil was placed in a beaker, and admixed with one of the saccharide powders while stirring. The resultant mixture had a fluidity when the addition of the saccharide powder was inexcessive, but became viscous and finally formed a mass as the addition was increased. When the mass was admixed with an additional amount of the saccharide powder, it became harder and crumbled. At this point, the oil holding capacity was calculated using the following equation:

$$\text{Oil holding capacity} = \frac{\text{Rapeseed oil (10 g)}}{\text{Saccharide powder (g)}} \times 100$$

The results are given in Table II.

Experiment 2-2

Comparison of emulsifying power

The emulsifying powers of several saccharide powders with a mean particle size of about 45–150 μ, prepared by the method in Experiment 2-1, were compared.

The emulsifying power was determined as follows: Two g of rapeseed oil was placed in a beaker, added with 2 g of each saccharide powder, and mixed by stirring with a glass rod. The resultant mixture was placed in a test tube equipped bearing a stop-cock, added with 30 ml water, mixed by shaking the test tube several times, and allowed to stand at room temperature overnight. The degree of white turbidity was determined by macroscopically observing the aqueous layer of the content.

After microscopic observation of the aqueous layer, the presence of the crystalline powder was not noted, but a number of oil droplets, about 2–5 μ, were observed. The higher the emulsifying powder was, the more the number of the oil droplets was.

The results are given in Table II.

These results evidently confirm that the crystalline alpha-maltose has superior oil holding capacity and emulsifying power, as well as an extremely high affinity to oil.

This feature is favorable to produce foodstuffs and ready-mix-type parenteral hyperalimentation that contain an oil-soluble substance, e.g. oil, fat, oil-soluble spice, oil-soluble coloring agent, oil-soluble vitamin, oil-soluble hormone, etc.

TABLE II

| Test No. | Alpha-maltose content (%) | Crystal | Oil holding capacity | Emulsifying power |
|---|---|---|---|---|
| 1 | 48.0 | Absent | 45 | — |
| 2 | 48.0 | Absent | 49 | — |
| 3 | 55.6 | Present | 110 | ++++ |
| 4 | 61.4 | Present | 126 | +++++ |
| 5 | 68.7 | Present | 95 | +++++ |
| 6 | 74.2 | Present | 73 | +++++ |
| 7 | 48.0 | Absent | 47 | — |
| 8 | 2.3 | Present | 53 | ++ |
| 9 | — | Present | 36 | + |
| 10 | — | Present | 40 | + |

Experiment 3

Comparison of low-moisture content processed food production

As an example of low-moisture content processed foods, chocolates were prepared with the saccharides as used in Experiment 2, and compared on work efficiency, organoleptic properties, and storage stability.

The chocolates were prepared in a known manner: Forty parts of cacao paste, 10 parts of cacao butter, and 50 parts of either of the saccharides powders were admixed, placed in a refiner, pulverized to homogeneity, added with 0.5 parts of lecithin, transferred into a conche, and homogenously dispersed by kneading at 60° C. overnight. Thereafter, the content was placed in a 31° C.-incubator, poured into a mold immediately before the cacao butter solidified, degassed with a vibrator, solidified by passing through a 10° C.-cooling tunnel for twenty minutes, removed from the mold, and packaged to obtain a product.

The work efficiency was represented as "superior", "slightly inferior", or "inferior" in relation to the difficulty confronted during the pulverization step.

The organoleptic test was carried out with a fifteen member-panel (ten adult men and five adult women), and the panel members were asked for their preference on the texture, melting properties and flavor in terms of "superior (+1)", "fair (0)", and "inferior (−1)". The quality of the chocolate was judges according to the total score obtained.

The stability of the chocolate was macroscopically checked after four month-standing at 25° C. under a relative humidity of 70%.

The results are given in table III.

TABLE III

| Test No. | Alpha-maltose isomer content (%) | Crystal | Work efficiency | Olganoleptic test | Stability | Integrated judge |
|---|---|---|---|---|---|---|
| 1 | 48.0 | Absent | Inferior | +7 | Moistened, softened, partly fat-bloomed | Control |
| 2 | 48.0 | Absent | Inferior | +10 | Moistened, softened, partly fat-bloomed | Control |
| 3 | 55.6 | Present | Superior | +42 | Unchanged | Present invention |
| 4 | 61.4 | Present | Superior | +45 | Unchanged | Present invention |
| 5 | 68.7 | Present | Superior | +45 | Unchanged | Present invention |
| 6 | 74.2 | Present | Superior | +45 | Unchanged | Present invention |
| 7 | 48.0 | Absent | Inferior | +8 | Moistened, softened, partly fat-bloomed | Control |
| 8 | 2.3 | Present | Slightly inferior | +24 | Partly sugar-bloomed | Control |
| 9 | — | Present | Superior | +26 | Partly sugar-bloomed | Control |
| 10 | — | Present | Slightly inferior | −41 | Fat- and sugar-bloomed | Control |

These results evidently confirm that in the manufacture of chocolate the crystalline alpha-maltose is superior in work efficiency, olganoleptic properties, and storage stability. Unlike the crystalline beta-maltose hydrate as disclosed in Japan Patent Kokai No. 31,650/84, the crystalline alpha-maltose is usable regardless of its degree of oil holding capacity to manufacture a high-quality chocolate.

The x-ray diffraction study of the chocolate containing the crystalline alpha-maltose also gave a diffraction spectrum characteristic to the crystalline alpha-maltose. Thus, it was confirmed that within the chocolate a substantial amount of the crystalline alpha-maltose incorporated is retained intact without undergoing changes in form, e.g. those effected by dissolution or melting.

Experiment 4

Effects of moisture content in high-purity maltose syrup on alpha-maltose crystallization The effects of moisture content of a high-concentration syrup on the crystallization of alpha-maltose were studied with "MALTOSE HHH", a crystalline beta-maltose powder having a maltose content of 99.7%, commercialized by Hayashibara Co. Ltd., Okayama, Japan.

Portions of "MALTOSE HHH" were dissolved in small amounts of water by heating, placed in an evaporator, and evaporated in vacuo to prepare syrups having different moisture contents. The syrups were then added with 2% aliquots of crystalline alpha-maltose seed, crystallized at 100° C. for five minutes, and aged at 70° C. for six hours. The obtaine blocks were cooled to room temperature, and their alpha-maltose isomer contents were then determined.

The results are given in Table IV.

TABLE IV

| Moisture in syrup (w/w %) | Crystal | Alpha-maltose isomer content (%) | Remarks |
|---|---|---|---|
| 2.1 | Present | 57.2 | Present invention |
| 3.5 | Present | 73.8 | Present invention |
| 5.0 | Present | 74.2 | Present invention |
| 7.1 | Present | 70.1 | Present invention |
| 8.6 | Present | 66.3 | Present invention |
| 9.3 | Present | 59.4 | Present invention |
| 12.3 | Present* | 25.2 | Control |
| 15.0 | Present* | 33.8 | Control |

Note:
*indicates that crystalline beta-maltose appeared.

These results confirm that in the crystallization of alpha-maltose the desirable moisture content of a high-purity maltose syrup is lower than 10 w/w %, in particular, 2.0 w/w % or higher but lower than 9.5 w/w %.

Experiment 5

Effect of temperature on crystallization of alpha-maltose

The effects of temperature on the crystallization of alpha-maltose were studied with "MALTOSE H", a crystalline beta-maltose hydrate powder having a maltose content of 91.5%, commercialized by Hayashibara Co., Ltd., Okayama, Japan.

Portions of "MALTOSE H" were dissolved with small amounts of water by heating, placed in an evaporator, and evaporated in vacuo to obtain syrups with a moisture content of 4.5 w/w %, which were then added with 2% aliquots of crystalline alpha-maltose seed, crystallized at 100° C. for five minutes, poured into aluminum trays, and aged at different temperatures within the range of 20°–140° C. for sixteen hours, followed by determination of the alpha-maltose isomer contents of the resultant blocks.

Separately, the coloring degree of each block was determined, and expressed by the absorbance difference (A420–720) calculated from the absorbances at 420 nm and 720 nm in 30 w/v % aqueous solution using 10 cm-cell.

The results are given in Table V.

These results evidently confirm that the temperature desirable for crystallization of alpha-maltose lies within the range of 50°–130° C., preferably, 60°–120° C. Also was confirmed that the coloring degree of crystalline alpha-maltose is variable with crystallization temperature, and that at a temperature exceeding 130° C. the coloring degree is drastically increased: The coloring degree at 140° C. was about 14–20-folds of that below 100° C.; about 7-folds of that at 120° C.; and about 3-folds of that at 130° C.

TABLE V

| Temperature (°C.) | Crystal | Alpha-maltose isomer content (%) | $A_{420-720}$ | Remarks |
|---|---|---|---|---|
| 20 | Present | 50.4 | 0.17 | Control |
| 40 | Present | 51.6 | 0.16 | Control |
| 50 | Present | 56.3 | 0.16 | Present invention |
| 60 | Present | 62.9 | 0.15 | Present invention |
| 70 | Present | 64.1 | 0.17 | Present invention |
| 80 | Present | 65.4 | 0.18 | Present invention |
| 100 | Present | 62.8 | 0.21 | Present invention |
| 120 | Present | 59.1 | 0.43 | Present invention |
| 130 | Present | 56.8 | 0.86 | Present invention |
| 140 | Present | 53.3 | 2.98 | Control |

Experiment 6

Effect of pressure on crystallization of alpha-maltose

The effects of pressure on the crystallization of alpha-maltose were studied with "MALTOSE HHH", a crystalline beta-maltose hydrate having a maltose content of 99.7%, commercialized by Hayashibara Co., Ltd., Okayama, Japan.

Portions of "MALTOSE HHH" were dissolved in small amounts of water by heating, placed in an evaporating vessel, boiled in vacuo to obtain syrups having a moisture content of 5.0 w/w/ %, which were then placed in a pressure container having an agitator, added with 2% aliquots of crystalline alpha-maltose seed, and crystallized at 70° C. by supplying an air with different pressure, i.e. 0–20 kg/cm2, under agitation. The contents were sampled, and their alpha-maltose isomer contents were then determined.

The results are given in Table VI.

TABLE VI

| Crystallization pressure (kg/cm$^2$) | Crystal | Alpha-maltose isomer content (%) |
|---|---|---|
| 0 | Present | 58.4 |
| 1 | Present | 61.6 |
| 2 | Present | 63.8 |
| 5 | Present | 65.3 |
| 10 | Present | 65.4 |

These results evidently confirm that elevated pressure, in particular, about 5 kg/cm2, accelerates alpha-maltose crystallization.

Experiment 7

Comparison of storage stability

The storage stability test was carried out with "MALTOSE HHH", a commercialized crystalline beta-maltose hydrate having a maltose content of 99.7%, a product of Hayashibara Co., Ltd., Okayama, Japan, and a crystalline alpha-maltose obtained from "MALTOSE HHH" by the method in Experiment 1, both in a finely divided form.

One hundred and fifth g of each sample was placed in an Erlenmeyer flask, which was then stoppered with stop-cock, and allowed to stand within a 50° C.-incubator. in the course of the incubation, the content was successively sampled, dissolved in water to give 30 w/w % aqueous solution, and determined for coloring degree and pH.

The coloring degree is represented by the difference of the absorbances of the solution at 420 nm and 720 nm measured with 10 cm-cell, i.e. (A420–720).

The results are given in Table VII.

These results evidently confirm that upon comparison under enclosing conditions the crystalline alpha-maltose is very stable but much less liable to cause browning and alteration than the commercialized crystalline beta-maltose hydrate.

Separately, portions of the crystalline beta-maltose hydrate and crystalline alpha-maltose were placed in Petri dishes, and then studied on their storage stabilities at 50° C. under ambient conditions. Browning or alteration was scarcely noted in the contents.

TABLE VII

| Period of storage (week) | | Sample | |
|---|---|---|---|
| | | Crystalline beta-maltose hydrate | Crystalline alpha-maltose |
| 0 | Coloring degree | 0.056 | 0.094 |
| | pH | 4.30 | 4.35 |
| 2 | Coloring degree | 0.145 | 0.096 |
| | pH | 3.56 | 4.40 |
| 4 | Coloring degree | 0.236 | 0.096 |
| | pH | 2.92 | 4.40 |
| 6 | Coloring degree | 0.310 | 0.096 |
| | pH | 2.87 | 4.40 |
| 10 | Coloring degree | 0.403 | 0.096 |
| | pH | 2.83 | 4.40 |

We found that crystalline alpha-maltose is superior to crystalline beta-maltose hydrate in water-solubility and instantly dissolvable even in a chilled water.

After subjection of an aqueous maltose solution, prepared by dissolving the crystalline alpha-maltose, to the action a crude human kidney alpha-glucosidase, prepared by the method as described in *The Journal of Biochemistry*, Vol.91, pp. 809–816 (1982), the maltose component in the aqueous solution was readily decomposed in glucose.

As explained with reference to the experiments, the crystalline alpha-maltose is scarcely browned or altered under enclosing conditions; instantly dissolvable in water; and, in solution, readily utilized by an in vivo enzyme. Thus, the crystalline alpha-maltose is suitable as the calorie source for the ready-mix-type parenteral hyperalimentation.

Several embodiments of the present invention will be described hereinafter.

EXAMPLE A

Production of crystalline alpha-maltose

Example A-1

A suspension of 1 part of potato starch and 10 parts of water was added with a commercialized liquefying bacterial alpha-amylase, gelatinized by heating to 90° C., and immediately heated to 130° C. to suspend the enzymatic reaction. Thus, a liquefied starch solution with a Dextrose Equivalent (DE) of about 0.5 was obtained. The starch solution was immediately cooled to 55° C., added with 100 units/g starch of isoamylase (EC 3.2.1.68) derived from a culture of *Pseudomonas amyloderamosa* ATCC 21262, and 50 units/starch of a soybean beta-amylasae (EC 3.2.1.2), commercialized by Nagase & Company, Ltd., Osaka, Japan, under trade name of "#1500", and saccharified at pH 5.0 for forty hours to obtain a high-purity maltose solution with a maltose content of 92.5%, which was then decolorized with activated carbon, followed by purification and deionization with ion exchange resins. The maltose solution was concentrated to 75%, fed to a crystallizer, added with 1% crystalline beta-maltose monohydrate seed, adjusted to 40° C., and gradually cooled to 30° C. in two days under gentle stirring conditions to obtain a crystal suspension. The crystals were separated from the suspension with a basket-type centrifuge, and washed by spraying a small amount of water to obtain a crystalline high-purity beta-maltose hydrate (purity 99.0%).

The high-purity maltose thus obtained was dissolved with a small amount of water by heating, placed in an evaporator, and evaporated in vacuo to prepare a syrup with a moisture content of 5.5 w/w %. The content was fed to a crystallizer, added with 1% crystalline alpha-maltose seed obtained by the method in Test No.6 in Experiment 1, crystallized at 100° C. for five minutes while stirring, poured into a plastic tray, and aged at 70° C. for six hours. The resultant block was then divided with a pulverizer, and dehydrated by fluidized-bed drying to obtain a pulverulent crystalline alpha-maltose with an alpha-maltose isomer content of 73.3% in the yield of about 92% based on the material crystalline high-purity beta-maltose hydrate.

The product is a white pulverulent sweetener having a mild sweetness. The product is favorably usable to manufacture foodstuffs, e.g. low-moisture content processed foods, foodstuffs containing an oil-soluble substance, alcoholic beverages, etc.; cosmetics; pharmaceuticals; and chemicals.

Example A-2

An aqueous solution of a high-purity maltose having a maltose content of 92.5%, prepared by the method in Example A-1, was concentrated in vacuo to give a moisture content of 20 w/w %, and sprayed through a nozzle, equipped at the top of a spraying tower, with a high-pressure pump. Simultaneously, 100° C. air was passed from the top of the tower towards a net conveyer carrying a fluidized crystalline alpha-maltose as the seed crystal, placed at the bottom of the tower, to collect the pulverized product on the net conveyer and also to fluidize the product out of the tower over a period of sixty minutes while passing a stream of 70° C. air upwards through the net. The resultant product was then placed in an ageing tower and aged for four hours in a stream of 70° C. air to obtain a pulverulent crystalline alpha-maltose with an alpha-maltose content of 66.2% in the yield of about 94% based on the material high-purity maltose.

The product is a white pulverulent sweetener having a mild sweetness. The product is favorably usable to manufacture foodstuff, e.g. low-moisture content food products such as chocolate, chewing gum, and cream paste; butter cream; "an"; "kyuhi"; fish meat product; alcoholic beverage, etc.

Example A-3

A suspension of 2 parts of corn starch and 10 parts of water was added with a commercialized bacterial liquefying alpha-amylase, gelatinized by heating to 90° C., and heated to 130° C. to suspend the enzymatic reaction in order to prepare a liquified starch solution having a DE of about 2. The starch solution was immediately cooled to 55° C., added with 120 units/g starch of isoamylase (EC 3.2.1.68), prepared from a culture of *Pseudomonas amyloderamosa* ATCC 21262, and 30 units/g starch of a soybean beta-amylase, saccharified at pH 5.0 for forty hours, and purified similarly as in Example A-1 to obtain a high-purity maltose solution with a maltose content of 88.6%, which was then concentrated in vacuo into a syrup with a moisture content of 3.5 w/w %. The syrup is then transferred into a crystallizer, added with 2.5% crystalline alpha-maltose seed obtained by the method in Example A-2, crystallized at 120° C. for ten minutes while stirring, poured into an aluminium tray, and aged at 70° C. for eighteen hours to obtain a solid. Similarly as in Example A-1, the solid was divided and dehydrated to obtain a pulverulent crystalline alpha-maltose with an alpha-maltose isomer content of 63.9% in the yield of about 94% based on the material high-purity maltose.

The product is a white pulverulent sweetener having a mild sweetness. The product is favorably usable to manufacture foodstuffs, e.g. low-moisture content processed foods such as chocolate, chewing gum, and cream paste; jam; custard cream; butter cream; "an"; bakery product; "kyuhi"; fish meat products; alcoholic beverage, etc.

Example A-4

A 45 w/w % aqueous solution of "HM-75", a starch sugar solution with a maltose content of 79.6%, commercialized by Hayashibara Col., Ltd., Okayama, Japan, was used as the feed solution. "XT-1022 E (Na+)", a strongly-acidic cation exchange resin, commercialized by Tokyo Chemical Industries, Kita-ku, Tokyo, Japan, was chosen and packed in water suspension in four 5.4 cm jacketed stainless steel columns to give respective bed depth of 5 m. The columns were cascaded to give a total bed depth of 20 m. The feed solution was admitted into the columns in an amount of 5 v/v % to the bed volume, and fractionated by passing 55° C. water at a space velocity of 0.13 through the columns while keeping the inner temperature of the column at 55° C. to obtain effluents. The maltose-rich fraction as separated from the effluents to obtain a high-purity maltose solution with a maltose content of 94.4%. After repeating these operations twenty cycles, the resultant high-purity maltose solutions were pooled, and concentrated in vacuo to obtain a syrup with a moisture content of 4.0 w/w %, which was then transferred into a crystallizer, added with 2% crystalline alpha-maltose seed obtained by the method in Example A-2, crystallized at 110° C. for twenty minutes under stirring, and granulated with a screw-type extrusion granulator. The resultant product was then placed in a drying chamber, and aged therein by dehydration in a stream of 80° C. air for two hours to obtain a pulverulent crystalline alpha-maltose with an alpha-maltose isomer content of 69.2% in the yield of about 93% based on the material high-purity maltose.

The product is a white pulverulent sweetener having a mild sweetness. As is the crystalline alpha-maltose obtained by the method in Example A-1, the product is favorably usable for foodstuffs, cosmetics, pharmaceuticals, chemicals, etc.

EXAMPLE B

Production of foodstuffs

Example B-1

Chewing gum

One hundred parts of chewing gum base was kneaded with 380 parts of a crystalline alpha-maltose having an alpha-maltose content of 61.4%, prepared by the method in Experiment 1, 1 part of L-asparatyl L-phneylalanine methyl ester, 10 parts of "COUPLING SUGAR®", a glycosylsucrose commercialized by Hayashibara Co., Ltd., Okayama, Japan, 1.5 parts of a beta-cyclodextrin inclusion complex with L-menthol, and a small amount of chlorophyll, fed to rolls, and cut into sheet in usual way.

The work efficiency during the manufacture was satisfactory.

The product is a tasty low-cariogenic chewing gum having an appropriate stretchability and desirable chewing properties. The product is stable over a long period of time.

Example B-2

Bittersweet chocolate

Forty parts of cacao paste and 5 parts of cacao butter were mixed with 55 parts of a crystalline alpha-maltose with an alpha-maltose content of 68.7%, prepared by the method in Experiment 1, and 0.2 parts of "α-G-Sweet", an alpha-glycosyl stevioside commercialized by Toyo Sugar Refining Co., Ltd., Tokyo, Japan. The mixture was fed to a refiner, and finely divided to homogeneity, added with 0.3 parts of lecithin, fed to a conche, kneaded within the conche, placed in an incubator, molded, and packaged to obtain a product.

The work efficiency during the manufacture was satisfactory. The amount(s) of cacao butter and/or lecithin which are relatively expensive may be favorably reduced by increasing the amount of the crystalline alpha-maltose.

The chocolate has excellent texture, melting properties, taste and flavor, but is free from sucrose harms.

Example B-3

Milk chocolate

Twenty-two parts of cacao paste and 15 parts of cacao butter were mixed with 35 parts of a crystalline alpha-maltose with an alpha-maltose content of 61.4%, prepared by the method in Experiment 1, and 10 parts of sucrose powder. The mixture was fed to a refiner, and finely disintegrated to homogeneity in usual way, added with 0.5 parts of lecithin, fed to a conche, kneaded within the conche, placed in an incubator, molded, and packaged to obtain a product.

The work efficiency during the manufacture was satisfactory.

The chocolate is tasty and excellent in texture and melting properties.

Example B-4

Cream paste

One thousand and two hundred parts of a crystalline alpha-maltose with an alpha-maltose content of 74.2%, prepared by the method in Experiment 1, 1,000 parts of shortening, 1 part of lecithin, 1 part of lemon oil, and 1 part of vanilla oil were mixed in usual way to obtain a cream paste.

The product is a tasty cream paste having a relatively low-sweetness and excellent in texture and melting properties.

Example B-5

Cream wafers

A cream paste, obtained by the method in Example B-4, was heated to 40°–45° C., and sandwiched between wafers.

The product is a high-quality cream wafers less susceptive to moisture-absorption and deformation.

Example B-6

Powdered oil

One hundred parts of a crystalline alpha-maltose with an alpha-maltose content of 55.6%, prepared by the method in Experiment 1, was gradually added with 80 parts of salad oil while stirring to obtain a powdered oil.

The product can be favorably used to prepare, e.g. hot cake mix, convenient soup granule, etc., as well as to cook potage soup, stew, dressing, mashed potato, and "cha-ahan (a Chinese dish of fried rice with eggs, shrimps, etc.)".

Example B-7

Granulated instant corn potage soup

Thirty parts of a crystalline alpha-maltose with an alpha-maltose content of 61.4%, prepared by the method in Experiment 1, was homogenously mixed with 9 parts of a heat-melted hardened vegetable oil, and added with 30 parts of a gelatinized corn powder, 15 parts of a gelatinized waxy cornstarch, 5 parts of monosodium glutamate, 8 parts of kitchen salt, 7 parts of defatted milk powder, and 0.5 parts of onion powder. The mixture was divided to homogeneity, sprayed with a small amount of an aqueous pullulan solution, fed to a granulator, and dried to obtain the captioned product.

Addition of hot water readily dissolves and disperses the product to give a tasty corn potage soup.

Example B-8

Vitamin A tablet

Fourteen parts of a crystalline alpha-maltose with an alpha-maltose content of 68.7%, prepared by the method in Experiment 1, was mixed with 1 part of vitamin A palmitate and 3 parts of cornstarch to homogeneity, and fed to a tabletting machine.

Each tablet contained about twenty thousand International Units of vitamin A palmitate.

The vitamin A in the table is less susceptive to oxidation, and the tablet per se is very resistant to deformation and cracking.

Example B-9

Butter cream

Eighty parts of fresh eggs was added with 100 parts of a pulverulent crystalline alpha-maltose, obtained by the method in Example A-1, creamed to give a mayonnaise-like appearance, mixing with 200 parts of butter while whipping, and flavored by adding a small amount of brandy when a satisfactory texture was obtained.

The product having a smooth texture and an appropriate sweetness is favorable for decorated cakes.

Example B-10

Custard cream

Five hundred parts of cornstarch, 900 parts of a pulverulent crystalline alpha-maltose obtained by the method in Example A-2, 5 parts of salt, and 1,400 part of fresh eggs were mixed under stirring, gradually added with 5,000 parts of a boiled milk, and stirred on a slow fire till the cornstarch was completely gelatinized to a translucent state. The mixture was cooled, and added with a small amount of vanilla flavor to obtain a custard cream.

The product with a gloss and a smooth texture was excellently tasty.

Example B-11

"Uiro (a sweet rice jelly)"

Ninety parts of rice powder, 20 parts of cornstarch, 120 parts of a pulverulent crystalline alpha-maltose obtained by the method in Example A-4, 4 parts of pullulan, and 1 part of "matcha (a ground tea)" was mixed to homogeneity, added with an appropriate amount of water, kneaded, placed in a vessel, and steamed for sixty minutes to prepare "matcha-uiro".

The product with a mild sweetness was excellent in gloss and texture.

Since the retrogradation of the amylaceous component was inhibited, the product was stable over a long period of time.

Example B-12

"An"

Two thousand parts of "nama-an" prepared from adzuki-beans were placed in a stainless steel pot, added with 900 parts of sucrose and 500 parts of a pulverulent crystalline alpha-maltose obtained by method method in Example A-4, heated under stirring, and kneaded in such a manner that the content did not scorch and stick to the bottom of the pot to obtain the captioned product.

The product was a tasty "an" excellent in texture.

Example B-13

Lemon jelly

In 200 parts of water was first dissolved 7 parts of agar by heating, then 150 parts of a pulverulent crystalline alpha-maltose obtained by the method in Example A-3. The mixture was then cooled to 65° C., added with 350 parts of a carbonated water containing small amounts of lemon flavor and coloring agent, poured into mold, and cooled therein to obtain a product.

The product was a tasty lemon jelly excellent in texture.

Example B-14

Sweetened condensed milk

One hundred parts of milk was pasteurized by heating at 80° C. for ten minutes, added with 16 parts of a pulverulent crystalline alpha-maltose obtained by the method in Example A-2, and concentrated in vacuo at 50°–55° C. Concentration was continued till the density of the mixture at 50° C. reached 1.305.

The product was a sweetened condensed milk having a mild sweetness and a high storage stability.

Example B-15

Jam

One thousand and five hundred parts of fresh strawberry, 640 parts of sucrose, 640 parts of a pulverulent crystalline alpha-maltose obtained by the method in Example A-1, 5 parts of pectin, and 1 part of citric acid were boiled down in a pot to obtain the captioned product.

In the product with an appropriate gel strength, the sour- and sweet-tastes were well balanced.

Example B-16

Hard candy

One hundred parts of "COUPLING SUGAR ®", a commercialized glycosylsucrose syrup, a product of Hayashibara Co., Ltd., Okayama, Japan, was added with 20 parts of a pulverulent crystalline alpha-maltose obtained by the method in Example A-2, dissolved by heating, boiled down to give a moisture content of lower than 1.5 w/w %, and molded in usual way to obtain a colorless hard candy having a satisfactory transparency.

The product was mildy sweet but not sticky.

Example B-17

"Synthetic sake"

In 3.9 liters of 35 v/v % ethanol was dissolved 400 g of a pulverulent crystalline alpha-maltose obtained by the method in Example A-2, 1.1 g of sodium glutamate, 7.2 g of citric acid, 1.4 g of 75 w/w % lactic acid, 0.6 g of sodium dihydrogen phosphate, 0.6 g of potassium dihydrogen phosphate, 0.6 g of calcium monohydrogen phosphate, 1.2 g of sodium succinate, 1.1 g of kitchen salt, 0.4 g of alanine, 0.3 g of glycine, and 4 ml of a liquid seasoning, and the mixture was added with water to give a total volume of 10 liters. The mixture was then separated from the sediment, filtered, pasteurized, and bottled to obtain the captioned product.

Since the crystalline alpha-maltose instantly dissolved in 35 v/v % ethanol, the work efficiency was very satisfactory.

The product was a mild "synthetic sake".

Example B-18

"Bettara-zuke (fresh radish pickles)"

Four parts of a pulverulent crystalline alpha-maltose obtained by the method in Example A-3, 0.05 parts of a Licorice extract, 0.008 parts of malic acid, 0.07 parts of sodium glutamate, 0.03 parts of potassium sorbate, and 0.2 parts of pullulan were homogeneously mixed to obtain a "bettarazuke-no-moto (a premix for bettarazuke)". Thirty kg of fresh radish was first pickled with kitchen salt, then with sucrose in conventional manner. Thereafter, the radish was further pickled in a seasoning solution prepared with 4 kg of the "bettara-zuke-no-moto" to obtain the captioned product.

The product was crisp, mildy sweet and excellent in color, gloss and flavor.

Example C

Production of ready-mix-type parenteral hyperalimentation

Example C-1

Injection

Fifty g aliquots of a pyrogen-free crystalline alpha-maltose, prepared by the method in Example A-1, were distributed in 600 ml-glass bottles, rubber-stoppered under sterile conditions, and cap-sealed to obtain a ready-mix-type injection.

Since the injection is stable over a long period of time even at room temperature, low temperature storage is not required. The water-solubility of the injection is satisfactory.

The injection is dissolved within the bottle with the addition of 500 ml sterilized distilled water, and administrated with a suitable injection method such as intravenous drip infusion.

Example C-2

Hemodialysis

Five hundred g aliquots of a pyrogen-free crystalline alpha-maltose, prepared by the method in Example A-2, were canned to obtain a ready-mix-type parenteral hyperalimentation for hemodialysis.

As is the product in Example C-1, this parenteral hyperalimentation is satisfactorily stable and soluble.

When "KINDALY SOLN-GF", a liquid preparation for hemodialysis, commercialized by Fuso Pharmaceutical Industries Ltd., Osaka, Japan, is diluted about thirty-times with a sterilized distilled water prior to its use, the preparation is dissolved along with the liquid preparation to give a final maltose concentration of about 0.5 w/w %. The solution so obtained is favorable to effect hemodialysis to the insulin-deficient person such as diabetic.

Example C-3

Injection

Two g aliquots of a composition, prepared with 1.985 parts of a pyrogen-free crystalline alpha-maltose obtained by the method in Example A-4, 0.01 part of thiamine, and 0.005 parts of calcium chloride, were placed in 30 ml-vials, rubber-stoppered, and cap-sealed to obtain a ready-mix-type injection.

As is the product in Example C-1, this injection is satisfactorily stable and soluble.

The injection is dissolved within the vial with the addition of 25 ml sterilized saline, and administered with a suitable injection method such as intravenous injection.

Example C-4

Injection

Five g aliquots of a composition, prepared with 4.96 parts of a pyrogen-free crystalline alpha-maltose obtained by the method in Example A-1, 0.03 parts of soybean oil, and 0.01 part of vitamin E acetate, were placed in 60 ml-vials, rubber-stoppered while injecting nitrogen, and capsealed to obtain a ready-mix-type injection.

As is the product in Example C-1, this injection is stable and excellent in solubility and emulsifying properties.

The injection is dissolved within the vial with the addition of 50 ml sterilized distilled water, and administrated with a suitable injection method such as intraperitoneal injection. The injection is also favorable for intubation feeding.

Example C-5

Intubation feeding

Twenty-four g aliquots of a composition, prepared with 20 parts of a crystalline alpha-maltose obtained by the method in Example A-3, 1.1 part of glycine, 0.18 parts of sodium glutamate, 1.2 parts of salt, 1 part of sodium citrate, 0.4 parts of calcium lactate, 0.1 part of magnesium carbonate, 0.01 part of thiamine, 0.01 part of riboflavin, were placed within laminated aluminium bags, followed by heat-sealing of the bags.

As is the product of Example C-1, this preparation is stable and excellently water-soluble.

One bag of the preparation is dissolved with the addition of about 300–500 ml water, and the administrated with intubation feeding into the nasal cavity, stomach, or intestine.

The preparation in solution is advantageously usable as parenteral hyperalimentation for domestic animals, as well as for human.

Example C-6

Intubation feeding

Twenty-five g aliquots of a composition, prepared with 580 parts of a crystalline alpha-maltose obtained by the method in Example A-4, 190 parts of dehydrated yolk, 209 parts of defatted milk, 4.4 parts of sodium chloride, 1.85 parts of potassium chloride, 4 parts of magnesium sulfate, 0.01 part of thiamine, 0.1 part of sodium ascorbate, 0.6 parts of vitamin E acetate, and 0.04 parts of nicotinamide, were placed within laminated aluminium bags, followed by heat-sealing of the bags.

As is the product in Example C-1, this preparation is stable and excellent in solubility and dispersibility.

One bag of the preparation is dissolved with the addition of about 150–300 ml of water, and then administrated with intubation feeding into the nasal cavity, esophagus, or stomach.

Example C-7

Intubation feeding

Four-hundred g aliquots of a composition, prepared with 16.5 parts of a crystalline alpha-maltose obtained by the method in Example A-1, 4.05 parts of sucrose, 3.2 parts of pulverized juice of "unshu-mikan (a tangerine)", 0.11 part of citric acid, 0.02 parts of ascorbic acid, 0.1 part of pulverized orange juice, and 0.02 parts of pullulan, were packed in screw-capped cans to obtain a ready-mix-type parenteral hyperalimentation.

As is the product in Example C-1, this preparation is stable and excellent in solubility.

About 25 of the preparation is dissolved with the addition of about 100–150 ml water, and then administrated by intubation feeding into the nasal cavity, or esophagus.

While there has been described what is at present considered to be the preferred embodiments of the invention, it will be understood that various modifications may be made therein, and it is intended to cover in the appended claims all such modifications as fall within the true spirit and scope of the invention.

We claim:

1. A process for producing crystalline alpha-maltose, comprising:
    preparing a high-concentration syrup with a moisture content lower than 10 w/w % from a high-purity maltose with a maltose content of 85 w/w % or higher based on the weight of the dry solids;
    crystallizing alpha-maltose from the syrup at a temperature within the range of 50°–130° C. in the presence of a seed crystal of alpha-maltose; and
    recovering the resultant crystalline alpha-maltose with an alpha-maltose isomer content of 55 w/w % or higher based on the weight of the dry solids.

2. The process in accordance with claim 1, wherein the moisture content of said high-concentration syrup is within the range of 2.0–9.5 w/w %.

3. The process in accordance with claim 1, wherein the crystallization step is carried out under a relatively high pressure.

4. The process in accordance with claim 1, wherein the crystallization step is carried out under dhydrating conditions.

5. The process in accordance with claim 1, wherein the crystallization step comprises a crystallization step and a subsequent ageing step.

6. The process in accordance with claim 1, wherein said alpha-maltose is in a finely divided form.

7. The process in accordance with claim 1, wherein the coloring degree of said crystalline alpha-maltose is lower than 1.0.

8. The process in accordance with claim 1, wherein said high-purity maltose has been obtained by:
    saccharifying starch either with a beta-amylase, or with a beta-amylase and a starch-debranching enzyme; and
    purifying the resultant hydrolysate.

9. The process in accordance with claim 1, wherein said high-purity maltose has been obtained by:
    fractionating a saccharide solution containing maltose with a strongly-acidic cation exchange resin in a salt form; and
    recovering the maltose-rich fraction.

10. The process in accordance with claim 1, wherein said crystalline alpha-maltose shows predominant diffraction angles ($2\theta$) of 12.6°, 20.3° and 21.9° upon x-ray diffraction analysis with CuK$\alpha$ ray.

11. A crystalline alpha-maltose, whenever produced by the process comprising:
    preparing a high-concentration syrup with a moisture content lower than 10 w/w % from a high-purity maltose with a maltose content of 85 w/w % or higher based on the weight of the dry solids;
    crystallizing alpha-maltose from the syrup at a temperature within the range of 50°–130° C. in the presence of a seed crystal of alphamaltose; and
    recovering the resultant crystalline alpha-maltose with an alpha-maltose isomer content of 55 w/w % or higher based on the weight of the dry solids.

12. The crystalline alpha-maltose in accordance with claim 11, wherein the moisture content of said high-concentration syrup is within the range of 2.0–9.5 w/w %.

13. The crystalline alpha-maltose in accordance with claim 11, wherein the crystallization step is carried out under a relatively high pressure.

14. The crystalline alpha-maltose in accordance with claim 11, wherein the crystalline step is carried out under dehydrating conditions.

15. The crystalline alpha-maltose in accordance with claim 11, wherein the crystallization step comprises a crystallization step and a subsequent ageing step.

16. The crystalline alpha-maltose in accordance with claim 11, wherein said alpha-maltose is in a finely divided form.

17. The crystalline alpha-maltose in accordance with claim 11, wherein the coloring degree of said crystalline alpha-maltose is lower than 1.0.

18. The crystalline alpha-maltose in accordance with claim 11, wherein said high-purity maltose has been obtained by:
   saccharifying starch either with a beta-amylase, or with a beta-amylase and a starch-debranching enzyme; and
   purifying the resultant hydrolysate.

19. The crystalline alpha-maltose in accordance with claim 11, wherein said high-purity maltose has been obtained by:
   fractionating a saccharide solution containing maltose with a strongly-acidic cation exchange resin in a salt form; and
   recovering the maltose-rich fraction.

20. The crystalline alpha-maltose in accordance with claim 11, which shows predominant diffraction angles ($2\theta$) of 12.6°, 20.3° and 21.9° upon x-ray diffraction analysis with CuK$\alpha$ ray.

21. A foodstuff having a moisture content lower than 10 w/w %, which contains a crystalline alpha-maltose, said crystalline alpha-maltose having at least 55 w/w % alpha-maltose isomer based on the weight of dry solids and having been prepared according to the process of claim 1.

22. The foodstuff in accordance with claim 21, wherein said crystalline apha-maltose has been crystallized from a high-purity maltose having a maltose content of 85 w/w % or higher based on the weight of the dry solids.

23. The foodstuff in accordance with claim 21, wherein said crystalline alpha-maltose has been crystallized in the presence of a seed crystal of alpha-maltose from a high-concentration syrup having a moisture content less than 10 w/w %.

24. The foodstuff in accordance with claim 21, containing an oil-soluble substance.

25. The foodstuff in accordance with claim 21, which is molded.

26. The foodstuff in accordance with claim 21, which is a sweetener.

27. The foodstuff in accordance with claim 21, which is a processed food.

28. The foodstuff in accordance with claim 21, which shows predominant diffraction angles ($2\theta$) of 12.6°, 20.3° and 21.9° upon x-ray diffraction analysis with Cuk$\alpha$ ray.

29. In a process for sweetening a foodstuff, comprising the step of incorporating maltose into said foodstuff, the improvement wherein said maltose in a crystalline alpha-maltose with an alpha-maltose isomer content of at least 55% based on the weight of dry solids and is produced in accordance with the process of claim 1.

30. The process in accordance with claim 29, wherein the step of incorporation is carried out without dissolving said crystalline alpha-maltose.

31. The process in accordance with claim 29, wherein said alpha-maltose has been crystallized from a high-purity maltose having a maltose content of 85 w/w % or higher based on the weight of the dry solids.

32. The process in accordance with claim 29, wherein said alpha-maltose has been crystallized in the presence of a seed crystal of alpha-maltose from a highconcentration syrup of high-purity maltose having a moisture content lower than 10 w/w %.

33. The process in accordance with claim 29, wherein the moisture content of said foodstuff is lower than 10 w/w %.

34. The process in accordance with claim 29, wherein said food-stuff contains an oil-soluble substance.

35. The process is accordance with claim 29, wherein said food-stuff is molded.

36. The process in accordance with claim 29, wherein said foodstuff shows predominant diffraction angles ($2\theta$) of 12.6°, 20.3° and 21.9° upon x-ray diffraction analysis with CuK$\alpha$ ray.

37. In a ready-mix parenteral hyperalimentation composition wherein maltose is used, the improvement wherein said maltose is a crystalline alpha-maltose.

38. The composition in accordance with claim 37, wherein the crystalline alpha-maltose contains at least 55 w/w % alpha-maltose isomer based on the weight of dry solids.

39. The composition in accordance with claim 37, wherein said crystalline alpha-maltose shows predominant diffraction angles ($2\theta$) of 12.6°, 20.3° and 21.9° upon x-ray diffraction analysis with CuK$\alpha$ ray.

40. The composition in accordance with claim 37, wherein said crystalline alpha-maltose has been crystallized from a high-purity maltose having a maltose content of 85 w/w % or higher based on the weight of the dry solids.

41. The composition in accordance with claim 37, wherein said crystalline alpha-maltose has been crystallized from a high-concentration syrup of a high-purity maltose having a moisture content lower than 10 w/w % by weight in the presence of seed crystal of alpha-maltose.

42. The composition in accordance with claim 37, wherein said composition contains at least one additional nutriment.

43. The composition in accordance with claim 42, wherein said at least one additional nutriment is selected from the group consisting of saccharide, protein, amino acid, and mineral.

44. The composition in accordance with claim 42, wherein said at least one additional nutriment is oil or fat.

45. The composition in accordance with claim 42, wherein said at least one additional nutriment is a vitamin.

46. The composition in accordance with claim 37, wherein said composition is packaged in a finely divided form.

47. The composition in accordance with claim 37, wherein said composition it is used in injection, intubation feeding, or hemodialysis.

* * * * *

UNITED STATES PATENT AND TRADEMARK OFFICE
CERTIFICATE OF CORRECTION

PATENT NO. : 4,816,445

DATED : March 28, 1989

INVENTOR(S) : Mitsuhashi et al.

It is certified that error appears in the above-identified patent and that said Letters Patent is hereby corrected as shown below:

| | |
|---|---|
| Column 2, line 45 | Delete "disolvable", insert therefor -- dissolvable -- |
| Column 3, line 4 | Delete "No. k20,174/79", insert therefor -- No.20,174/79 -- |
| Column 3, lines 24-25 | Delete "alphamaltose", insert therefor -- alpha-maltose -- |
| Column 3, line 38 | Delete "alphamaltose", insert therefor -- alpha-maltose -- |
| Column 3, line 42 | Delete "alphamaltose", insert therefor -- alpha-maltose -- |
| Column 6, line 59-60 | Delete "w/w%", insert therefor -- 10 w/w % -- |
| Column 7, line 14 | Delete "alphamaltose", insert therefor -- alpha-maltose -- |
| Column 7, line 34-35 | Delete "15 ww %", insert therefor -- 15 w/w % -- |
| Column 8, line 59 | Delete "beef tallw", insert therefor -- beef tallow -- |
| Column 11, line 63 | After "in order", insert -- to -- |
| Column 12, lines 3&18 | Delete "alphamaltose", insert therefor -- alpha-maltose -- |
| Column 18, line 60 | Delete "kyuhi", insert therefor -- gyuhi -- |
| Column 19, line 26 | Delete "kyuhi", insert therefor -- gyuhi -- |

UNITED STATES PATENT AND TRADEMARK OFFICE
CERTIFICATE OF CORRECTION

PATENT NO. : 4,816,445
DATED : March 28, 1989
INVENTOR(S) : MITSUHASHI et al.

It is certified that error appears in the above-identified patent and that said Letters Patent is hereby corrected as shown below:

Con't

| | |
|---|---|
| Column 24, line 64 | delete "capsealed", insert therefor -- cap-sealed -- |
| Column 26, line 23 | Delete "dhydrating", insert therefor -- dehydrating -- |
| Column 26, line 58 | Delete "alphamaltose", insert therefor -- alpha-maltose -- |
| Column 28, lines 10 & 11 | Delete "highconcentration", insert therefor -- high concentration -- |

Signed and Sealed this

Twelfth Day of November, 1991

Attest:

HARRY F. MANBECK, JR.

*Attesting Officer*     *Commissioner of Patents and Trademarks*